(12) United States Patent
Wakamatsu et al.

(10) Patent No.: US 9,968,766 B2
(45) Date of Patent: May 15, 2018

(54) TRANSDERMAL ABSORPTION SHEET AND METHOD OF MANUFACTURING TRANSDERMAL ABSORPTION SHEET

(71) Applicant: FUJIFILM Corporation, Tokyo (JP)

(72) Inventors: Satoshi Wakamatsu, Kanagawa (JP); Koki Kabata, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 70 days.

(21) Appl. No.: 15/299,563

(22) Filed: Oct. 21, 2016

(65) Prior Publication Data

US 2017/0036003 A1    Feb. 9, 2017

Related U.S. Application Data

(63) Continuation of application No. PCT/JP2015/060454, filed on Apr. 2, 2015.

(30) Foreign Application Priority Data

May 15, 2014 (JP) .................................. 2014-101752

(51) Int. Cl.
*A61M 37/00* (2006.01)

(52) U.S. Cl.
CPC ........ *A61M 37/00* (2013.01); *A61M 37/0015* (2013.01); *A61M 2037/0023* (2013.01);
(Continued)

(58) Field of Classification Search
CPC .. A61M 2037/0023; A61M 2037/0046; A61M 2037/0053; A61M 2207/10; A61M 37/00; A61M 37/0015
See application file for complete search history.

(56) References Cited

U.S. PATENT DOCUMENTS

| 2008/0269685 | A1 | 10/2008 | Singh et al. |
| 2011/0192562 | A1 | 8/2011 | Motoi et al. |
| 2012/0078189 | A1* | 3/2012 | Ogawa .............. A61M 37/0015 604/173 |

FOREIGN PATENT DOCUMENTS

| JP | 2010-142473 A | 7/2010 |
| JP | 2010-233674 A | 10/2010 |

(Continued)

OTHER PUBLICATIONS

Air Embolism by Kivi, R. [online] retrieved on Feb. 17, 2018 from: https://www.healthline.com/health/air-embolism; Sep. 2015; 2 pages. (Year: 2015).*

(Continued)

*Primary Examiner* — Ernst V Arnold
(74) *Attorney, Agent, or Firm* — Sughrue Mion, PLLC

(57) ABSTRACT

To provide a transdermal absorption sheet with which control of a dissolution rate and suppression of drug diffusion can be achieved, and a method of manufacturing the transdermal absorption sheet. A transdermal absorption sheet 100 is provided with a sheet portion 116, a plurality of frustum portions 114 that is disposed on the sheet portion 116, and needle portions 112 that are disposed on the frustum portions 114, each of the plurality of needle portions 112 includes a first layer 120 containing a drug and a second layer 122 not containing a drug, and at least one of the plurality of needle portions 112 contains an air bubble 124.

15 Claims, 17 Drawing Sheets

(52) U.S. Cl.
CPC ............... *A61M 2037/0046* (2013.01); *A61M 2037/0053* (2013.01); *A61M 2207/10* (2013.01)

(56) References Cited

FOREIGN PATENT DOCUMENTS

| | | |
|---|---|---|
| JP | 2011-078617 A | 4/2011 |
| JP | 2013-153866 A | 8/2013 |
| WO | 2008/130587 A2 | 10/2008 |

OTHER PUBLICATIONS

Communication dated May 22, 2017, from the European Patent Office in counterpart European Application No. 15792241.0.
International Search Report for PCT/JP2015/060454 dated Jul. 7, 2015.
Written Opinion for PCT/JP2015/060454 dated Jul. 7, 2015.

* cited by examiner

TRANSDERMAL ABSORPTION SHEET AND METHOD OF MANUFACTURING TRANSDERMAL ABSORPTION SHEET

CROSS-REFERENCE TO RELATED APPLICATIONS

This application is a Continuation of PCT International Application No. PCT/JP2015/060454 filed on Apr. 2, 2015, which claims priority under 35 U.S.C. § 119(a) to Japanese Patent Application No. 2014-101752 filed on May 15, 2014. Each of the above applications is hereby expressly incorporated by reference, in their entirety, into the present application.

BACKGROUND OF THE INVENTION

1. Field of the Invention

The present invention relates to a transdermal absorption sheet and a method of manufacturing the transdermal absorption sheet.

2. Description of the Related Art

In recent years, transdermal absorption sheets in which need e-shaped projections (also referred to as fine needles or microneedles) containing a drug are formed have been used in order to deliver the drug into the skin. In general, the transdermal absorption sheet is pressed to the skin to insert the needle-shaped projections into the skin, thereby delivering the drug in the needle-shaped projections into the skin.

As a method of manufacturing the transdermal absorption sheet. JP2011-078617A discloses a method using a mold having a through hole formed in the bottom of a needle-shaped recess, in which a base solution that is a polymer solution containing no drug is added after a drug solution that is a polymer solution containing a drug is added to the needle-shaped recess of the mold and the drug solution in the needle-shaped recess is dried.

SUMMARY OF THE INVENTION

In a case where an air bubble remains in the needle-shaped projections in the transdermal absorption sheet, a variation occurs in the content of the drug in the needle-shaped. projections. In addition, needle-shaped projections may be lost in a peeling-off step, and needle-shaped projections may thus not bear a load during puncture and be broken, thereby resulting in a puncture error.

Regarding the transdermal absorption sheet, there is a demand for controlling a rate of transmission of a drug into the skin, that is, a dissolution rate of the needle-shaped projection containing the drug in the skin, or a demand for suppressing drug solution diffusion to the base solution.

The inventors have found that in a case where an air bubble is disposed in the needle-shaped projection, the dissolution rate is improved and the air bubble becomes a barrier for drug diffusion, and accomplished the invention.

The invention is contrived in view of the circumstances, and an object thereof is to provide a transdermal absorption sheet with which control of a dissolution rate and. suppression of drug diffusion can be achieved, and a method of manufacturing the transdermal absorption sheet.

According to an embodiment, a transdermal absorption sheet comprises a flat plate-shaped sheet portion; a plurality of frustum portions which are disposed on the sheet portion and in each of which a larger bottom surface is connected to the sheet portion; and a plurality of tapered-shaped needle portions which are disposed on the plurality of frustum portions and in each of which a bottom surface is connected to a smaller bottom surface of the frustum portion, wherein each of the plurality of needle portions includes a first layer containing a predetermined amount of a drug and a second layer not containing a predetermined amount of a drug, and at least one of the plurality of needle portions contains an air bubble.

The air bubble is preferably disposed between the first layer and the second layer.

The air bubble preferably has a diameter of 1 µm to 50 µm.

The needle portion preferably has a cone shape.

A tapered needle-shaped portion and a cylindrical body portion preferably configure the needle portion.

An angle a formed between a side surface of the frustum portion and a surface parallel to a front surface of the sheet portion is preferably 10° to 60°.

The frustum portion preferably has a height of 10 µm to 1,000 µm.

The drug is preferably a peptide, a protein, a nucleic acid, a polysaccharide, a vaccine, a medical compound belonging to a water-soluble low-molecular-weight compound, or a cosmetic component.

According to another embodiment, a method of manufacturing a transdermal absorption sheet comprises in this order a drug solution filling step of filling needle-shaped recesses of a mold having the needle-shaped recesses arranged two-dimensionally with a drug solution that is a polymer solution containing a drug, a drug solution drying step of drying the drug solution filled in the needle-shaped recesses to form a first layer containing a drug, a base solution filling step of filling the needle-shaped recesses with a base solution that is a polymer solution not containing a drug on the first layer while incorporating an air bubble, a base solution drying step of drying the base solution to form a second layer not containing a drug on the first layer, and a peeling-off step of peeling off the first layer and the second layer from the mold, and the base solution drying step is performed in an environment with a temperature of 1° C. to 10° C.

The method preferably comprises a step of subjecting the drug solution to deaeration before the drug solution filling step.

The needle-shaped recess of the mold preferably has a through hole at a tip end thereof.

In the drug solution drying step, the drying is preferably performed in a calm state.

In the drug solution filling step, a nozzle that discharges the drug solution is preferably pressed to the mold to perform scanning on the mold, and the needle-shaped recesses are preferably filled with the drug solution from the nozzle while a pressing force of the nozzle with respect to the mold is controlled.

In the drug solution filling step, a nozzle that discharges the drug solution is preferably pressed to the mold to perform scanning on the mold, and the needle-shaped recesses are preferably filled with the drug solution from the nozzle while a pressing distance of the nozzle with respect to the mold is controlled.

In the drug solution filling step, the amount of the drug solution to be filled is preferably the same as a total volume of the needle-shaped recesses.

The invention provides a transdermal absorption sheet with which control of a dissolution rate and suppression of drug diffusion can be achieved, and a method of manufacturing the transdermal absorption sheet.

DESCRIPTION OF TILE PREFERRED EMBODIMENTS

Figure 1:
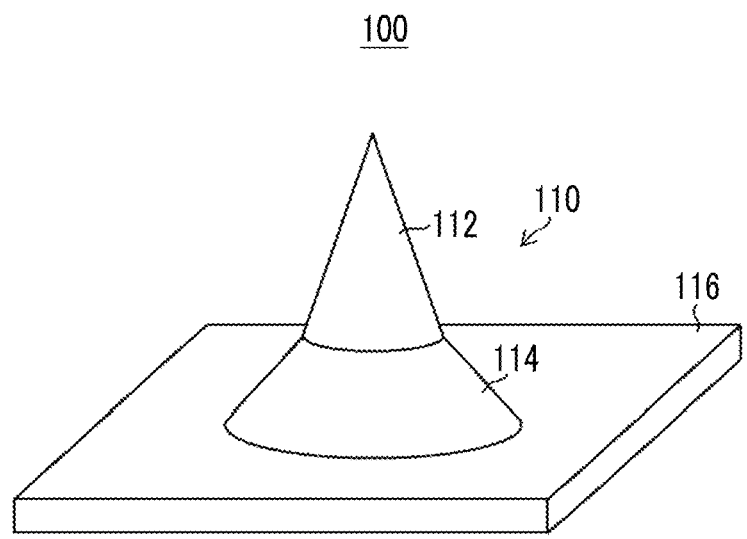
FIG. 1 is a perspective view of a transdermal absorption sheet having a needle-shaped projection.

Hereinafter, preferred embodiments of the invention will be described with reference to the accompanying drawings. The invention will be described with the following preferred embodiments. Modifications can be made by many methods without departing from the scope of the invention, and embodiments other than the embodiments can be used. Accordingly, all of the modifications within the scope of the invention are included in the claims.

Here, in the drawings, the parts represented by the same references are the same elements having the same functions. In this description, in a case where a numerical value range is expressed using the form of ". . . to . . . ", the numerical values of the upper limit and the lower limit shown in the form of ". . . to . . . " are also included in the numerical value range.

Figure 2:
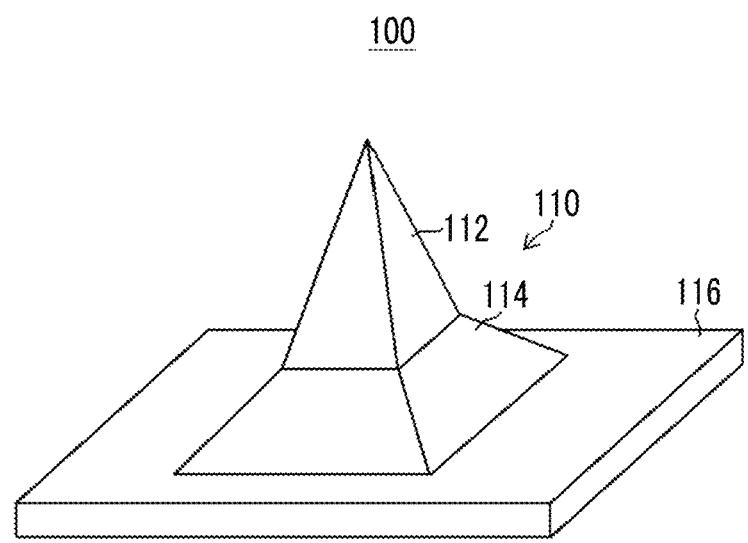
FIG. 2 is a perspective view of a transdermal absorption sheet having a needle-shaped projection having a different shape.

A transdermal absorption sheet manufactured in this embodiment will be described. FIGS. 1 and 2 each illustrates a needle-shaped projection 110 (also referred to as a fine needle or a microneedle) that is a partially enlarged view of a transdermal absorption sheet 100.

The transdermal absorption sheet 100 delivers a drug into the skin by being attached to the skin. As illustrated in FIG. 1, the transdermal absorption sheet 100 has a tapered-shaped needle portion 112, a frustum portion 114 connected to the needle portion 112, and a flat plate-shaped sheet portion 116 connected to the frustum portion 114. The tapered-shaped. needle portion 112 and the frustum portion 114 configure the needle-shaped projection 110.

A plurality of frustum portions 114 is formed on a front surface of the sheet portion 116 (only one frustum portion 114 is shown in FIG. 1). Among two end surfaces of the frustum portion 114, an end surface (lower base) having a larger area is connected to the sheet portion 116. Among the two end surfaces of the frustum portion 114, an end surface (upper base) having a smaller area is connected to the needle portion 112. That is, among the two end surfaces of the frustum portion 114, an end surface in a direction in which it is separated from the sheet portion 116 has a smaller area. Since a surface having a larger area in the needle portion 112 is connected to the end surface having a smaller area in the frustum portion 114, the needle portion 112 has a gradually tapered shape in a direction in which it is separated from the frustum portion 114.

In FIG. 1, the frustum portion 114 has a truncated circular cone shape, and the needle portion 112 has a cone shape. The shape of a tip end of the needle portion 112 can be appropriately changed to a curved surface having a radium of curvature of 0.01 µm to 50 µm, a flat surface, or the like in accordance with the degree of insertion of the needle portion 112 into the skin.

FIG. 2 illustrates a needle-shaped projection 110 having a different shape. In FIG. 2, the frustum portion 114 has a truncated quadrangular pyramid shape, and the needle portion 112 has a quadrangular pyramid shape.

Figure 3:
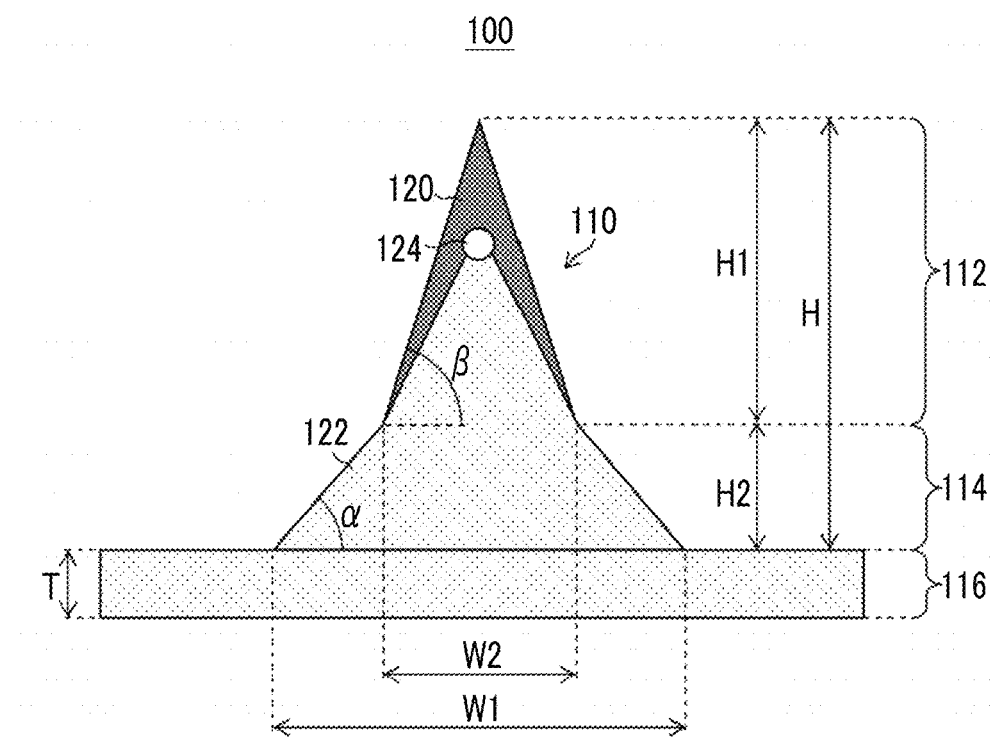
FIG. 3 is a cross-sectional view of the needle-shaped projection of the transdermal absorption sheet illustrated in FIGS. 1 and 2.

FIG. 3 is a cross-sectional view of the transdermal absorption sheet 100 illustrated in FIGS. 1 and 2. As illustrated in FIG. 3, a first layer 120 containing a predetermined amount of a drug and a second layer 122 not containing a predetermined amount of a drug configure the transdermal absorption sheet 100. Here, the expression "containing a predetermined amount of a drug" means containing the drug in an amount such that medicinal effects are exhibited when puncture is performed on a body surface. The expression "not containing a predetermined amount of a drug" means that the drug is not contained in an amount such that medicinal effects are exhibited, and the range of the amount of the drug includes a range from 0, indicating that the drug is not contained at all, to an amount in which medicinal effects are not exhibited. The first layer 120 containing a drug is formed at a tip end (the tip end of the needle portion 112) of the needle-shaped projection 110. The drug can be efficiently delivered into the skin by forming the first layer 120 at the tip end of the needle-shaped projection 110. Hereinafter, the expression "containing a predetermined amount of a drug" will be referred to as "containing a drug", and the expression "not containing a predetermined amount of a drug" will be referred to as "not containing a drug", if necessary.

The second layer 122 not containing a drug is formed in a portion excluding the first layer 120 in the needle portion 112. The second layer 122 configures the frustum portion 114. The second layer 122 configures the sheet portion 116. Division of the first layer 120 and the second layer 122 configuring the needle portion 112, the frustum portion 114, and the sheet portion 116 can be appropriately set.

A thickness T of the sheet portion 116 is in a range of 10 µm to 2,000 µm, and preferably in a range of 10 µm to 1,000 µm. A width W1 of the portion (lower base) in which the frustum portion 114 and the sheet portion 116 are in contact with each other is in a range of 100 µm to 1,500 µm, and preferably in a range of 100 µm to 1,000 µm. A width W2 of the portion (upper base) in which the frustum portion 114 and the needle portion 112 are in contact with each other is in a range of 100 µm to 1,500 µm, and preferably in a range of 100 µm to 1,000 µm. The width W1 and the width W2 satisfy the relationship of W1>W2 within the above numerical value range.

A height H of the needle-shaped projection 110 is in a range of 100 µm to 2,000 µm, and preferably in a range of 200 µm to 1,500 µm. In addition, H1/H2 that is a ratio of a height H1 of the needle portion 112 to a height H2 of the frustum portion 114 is in a range of 1 to 10, and preferably in a range of 1.5 to 8. The height 112 of the frustum portion 114 is preferably in a range of 10 µm to 1,000 µm.

An angle α formed between a side surface of the frustum portion 114 and a surface parallel to the front surface of the sheet portion 116 is in a range of 10° to 60°, and preferably in a range of 20° to 50°. An angle β formed between a side surface of the needle portion 112 and a surface parallel to the upper base of the frustum portion 114 is in a range of 45° to 85°, and preferably in a range of 60° to 80°.

The angle β is preferably equal to or larger than the angle α. This is because the needle-shaped projection 110 is easily inserted into the skin.

In this embodiment, an air bubble 124 is disposed in the needle portion 112. The diameter of the air bubble 124 is preferably 1 µm to 100 µm. In consideration of the possibility that the needle-shaped projections may not bear a load during puncture and be broken, thereby resulting in a puncture error, the diameter of the air bubble is preferably 1 µm to 50 µm, and more preferably 1 µm to 10 µm. The volume of the air bubble 124 is preferably 2% or less of the volume of the needle-shaped projection 110. One or more air bubbles 124 may be included in one needle portion 112. The dissolution rate of the first layer 120 containing a drug can be promoted by adjusting the diameter of the air bubble 124 within a range of 1 µm to 100 µm.

Figure 4A:
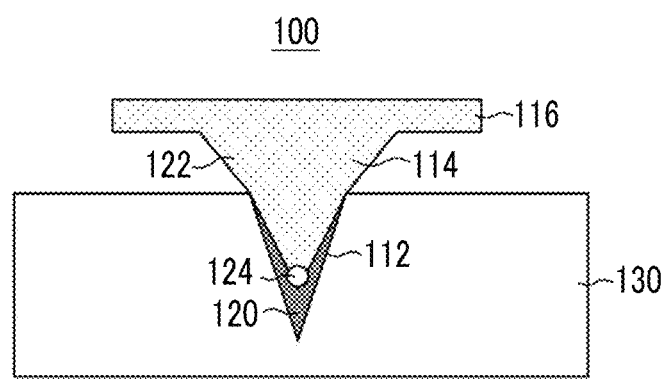
FIG. 4A is an explanation drawing illustrating a state in which a drug of the transdermal absorption sheet is delivered into the skin.
Figure 4B:
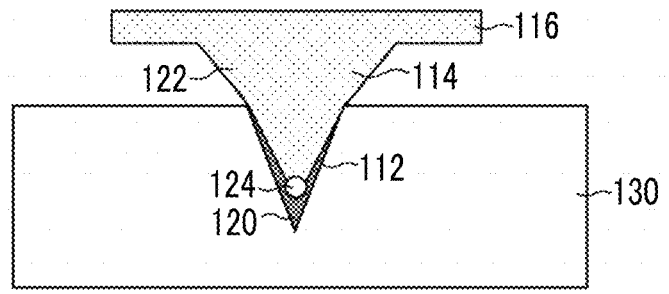
FIG. 4B is an explanation drawing illustrating a state in which a drug of the transdermal absorption sheet is delivered into the skin.
Figure 4C:
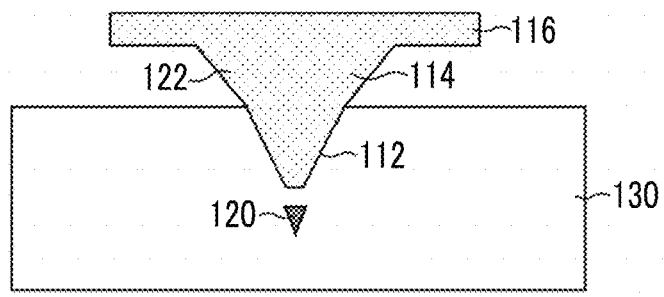
FIG. 4C is an explanation drawing illustratimg a state in which a drug of the transdermal absorption sheet is delivered into the skin.

FIGS. 4A to 4C are explanation drawings illustrating a state in which the drug of the transdermal absorption sheet is delivered into the skin. FIG. 4A illustrates a state Immediately after sticking of the transdermal absorption sheet 100 into a skin 130. The needle portion 112 is positioned in the skin 130, and the first layer 120 containing a drug and the air bubble 124 disposed in the needle portion 112 are disposed in the skin 130.

FIG. 4B illustrates a state in which several minutes have elapsed after sticking of the transdermal absorption sheet 100 into the skin 130. The first layer 120 configuring the needle portion 112 is dissolved, and the drug contained in the first layer 120 is delivered into the skin 130. Since the first layer 120 is dissolved, the size of the first layer 120 is reduced compared to the size immediately after sticking of the sheet into the skin 130.

FIG. 4C illustrates a state in which several minutes have elapsed from the state of FIG. 4B. In a case where the first layer 120 configuring the needle portion 112 is further dissolved and the first layer 120 is reduced in size until reaching the air bubble 124, the first layer 120 and the second layer 122 are separated from each other. The whole periphery of the first layer 120 contacts with the skin 130. Since the contact area between the first layer 120 and the skin 130 is increased, the dissolution rate of the first layer 120 can be promoted.

The position where the air bubble 124 is disposed may be in the needle portion 112. Furthermore, the air bubble 124 is preferably disposed at the boundary between the first layer 120 and the second layer 122 in the needle portion 112. In a case where the air bubble 124 is disposed at the boundary between the first layer 120 and the second layer 122, the first layer 120 and the second layer 122 can be quickly separated from each other. Here, the expression "the air bubble 124 is disposed at the boundary between the first layer 120 and the second layer 122" means that the air bubble 124 is in contact with the first layer 120 and the second layer 122. In addition, in a case where the air bubble 124 is disposed at the boundary, the air bubble 124 particularly preferably enters into the second layer 122, not into the first layer 120. This is because a variation may occur in the dose of the drug in a case where the air bubble 124 enters into the first layer 120. In addition, the air bubble 124 is preferably positioned on the center axis of the needle portion 112 and contained in the needle portion 112. The minimum distance from the side surface of the needle portion 112 to the surface of the air bubble 124 is preferably 10 μm or greater.

In a case where a plurality of air bubbles 124 is disposed in the needle portion 112, one air bubble 124 may be disposed at the boundary between the first layer 120 and the second layer 122.

The air bubble 124 may be disposed in at least one of a plurality of needle portions 112 formed in one transdermal absorption sheet 100. In a case where needle portions 112 containing the air bubbles 124 and needle portions 112 containing no air bubbles 124 are mixed in one transdermal absorption sheet 100, the dissolution rate of the drug of one transdermal absorption sheet 100 can be controlled. The needle portion 112 containing the air bubble 124 may be disposed at a certain position in one transdermal absorption sheet 100, or at a random position in one transdermal absorption sheet 100.

Figure 5:
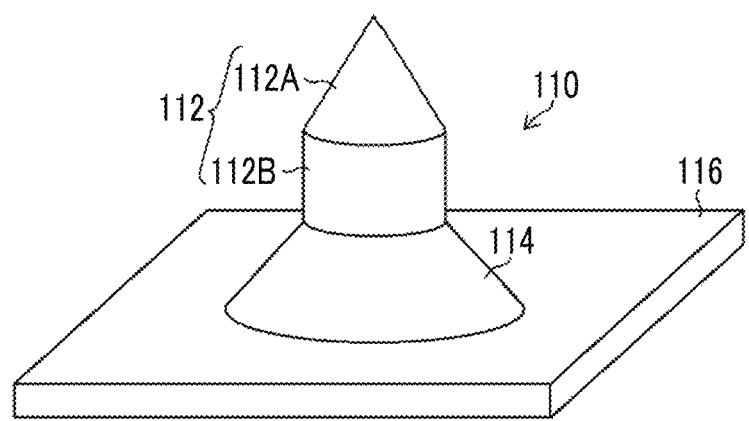
FIG. 5 is a perspective view of a transdermal absorption sheet having a needle-shaped. projection having a different shape.
Figure 6:
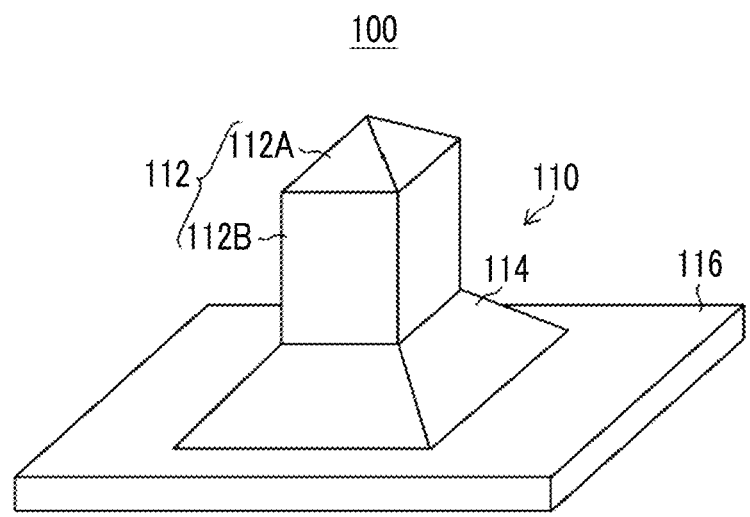
FIG. 6 is a perspective view of a transdermal absorption sheet having a needle-shaped projection having a different shape.

FIGS. 5 and 6 each illustrates a needle-shaped projection 110 having a different shape. In the transdermal absorption sheet 100 illustrated in FIGS. 1 and 5 and the transdermal absorption sheet 100 illustrated in FIGS. 2 and 6, the frustum portions 114 have the same shape, and the needle portions 112 have different shapes. Each of the needle portions 112 illustrated in FIGS. 5 and 6 has a tapered needle-shaped portion 112A and a cylindrical body portion 112B. A bottom surface of the needle-shaped portion 112A and an end surface of the body portion 112B are connected to each other. Among end surfaces of the body portion 112B, an end surface that is not connected to the needle-shaped portion 112A is connected to the upper base of the frustum portion 114.

The needle-shaped portion 112A and the body portion 1123 illustrated in FIG. 5 have a cone shape and a columnar shape, respectively. The needle-shaped portion 112A and the body portion 112B illustrated in FIG. 6 have a quadrangular pyramid shape and a quadrangular prism shape, respectively.

Since the needle portion 112 has the body portion 112B, the needle portion 112 has a shape having a constant width in a direction in which it is separated from the frustum portion 114. The needle-shaped portion 112A of the needle portion 112 has a gradually tapered shape in a direction in which it is separated from the body portion 112B. In the cylindrical body portion 112B, two end surfaces thereof opposed to each other have almost the same area. The needle portion 112 has a tapered shape as a whole. The shape of a tip end of the needle portion 112 can be appropriately changed to a curved surface having a radium of curvature of 0.01 μm to 50 μm, a flat surface, or the like in accordance with the degree of insertion of the needle portion 112 into the skin.

Figure 7:
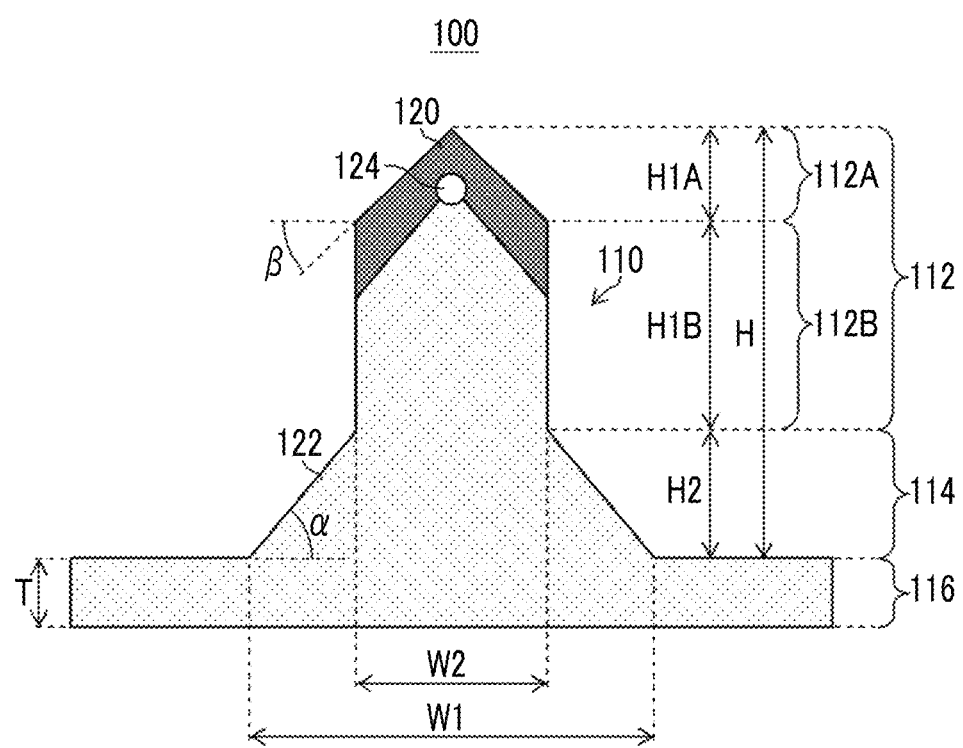
FIG. 7 is a cross-sectional view of the needle-shaped projection of the transdermal absorption sheet illustrated in FIGS. 5 and 6.

FIG. 7 is a cross-sectional view of the transdermal absorption sheet 100 illustrated in FIGS. 5 and 6. As illustrated in FIG. 7, a first layer 120 containing a drug and a second layer 122 not containing a drug configure the transdermal absorption sheet 100. The first layer 120 containing a drug is formed at a tip end (the tip end of the needle portion 112) of the needle-shaped projection 110. The drug can be efficiently delivered into the skin by forming the first layer 120 at the tip end of the needle-shaped projection 110.

The second layer 122 not containing a drug is formed in a portion excluding the first layer 120 in the needle portion 112. The second layer 122 configures the frustum portion 114. The second layer 122 configures the sheet portion 116. Division of the first layer 120 and the second layer 122 configuring the needle portion 112, the frustum portion 114, and the sheet portion 116 can be appropriately set.

A thickness T of the sheet portion 116, a width W1 of the lower base of the frustum portion 114, a width W2 of the upper base of the frustum portion 114, a height H of the needle-shaped projection 110, and a height 112 of the frustum portion 114 can be adjusted to the same lengths as those of the transdermal absorption sheet 100 illustrated in FIG. 3. H1/H2 that is a ratio of a height H1 of the needle portion 112 to the height H2 of the frustum portion 114 can be adjusted to the same ratio as that of the transdermal absorption sheet 100 illustrated in FIG. 3.

H1B/H1A that is a ratio of a height H1B of the body portion 112B to a height H1A of the needle-shaped portion 112A is in a range of 0.1 to 4, and preferably in a range of 0.3 to 2.

An angle α formed between a side surface of the frustum portion 114 and a surface parallel to the front surface of the sheet portion 116 is in a range of 10° to 60°, and preferably in a range of 20° to 50°. An angle p formed between a side surface of the needle-shaped portion 112A and a surface parallel to the end surface of the body portion 112B is in a range of 45° to 85°, and preferably in a range of 60° to 80°.

The angle β is preferably equal to or larger than the angle α. This is because the needle-shaped projection 110 is easily inserted into the skin.

In this embodiment, an air bubble 124 is disposed in the needle portion 112. The diameter of the air bubble 124 is preferably 1 μm to 100 μm. In consideration of the possibility that the needle-shaped projections may not bear a load during puncture and be broken, thereby resulting in a puncture error, the diameter of the air bubble is preferably 1 μm to 50 μm, and more preferably 1 μm to 10 μm. One or more air bubbles 124 may be included in one needle portion 112. The dissolution rate of the first layer 120 containing a drug can be promoted by adjusting the diameter of the air bubble 124 within a range of 1 μm to 100 μm.

In this embodiment, the transdermal absorption sheets 100 having the needle portions 112 illustrated in FIGS. 1, 2, 5, and 6 are show, but the transdermal absorption sheet 100 is not limited to these shapes.

(Mold)

Figure 8A:
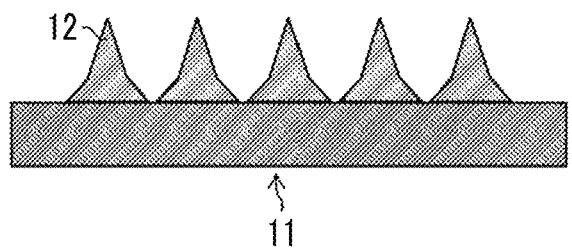
FIG. 8A is a process drawing of a method of manufacturing a mold.
Figure 8B:
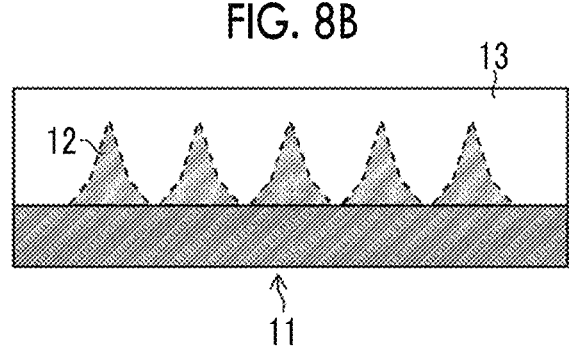
FIG. 8B is a process drawing of a method of manufacturing a mold.
Figure 8C:
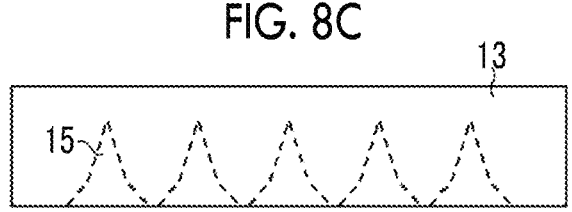
FIG. 8C is a process drawing of a method of manufacturing a mold.

FIGS. 8A to 8C are process drawings of the production of a mold (form).

As illustrated in FIG. 8A, first, an original plate for producing a mold for manufacturing a transdermal absorption sheet is produced.

There are two methods for producing the original plate 11. A first method includes applying a photoresist to a Si substrate, exposure, and developing. In addition, etching by reactive ion etching (RIE) or the like is performed to produce a plurality of projections 12, each having the same shape as the needle-shaped projection of the transdermal absorption sheet, in arrays on a front surface of the original plate 11. When etching such as RIE is performed in order to form the projects 12 on the front surface of the original plate 11, the projections 12 can be formed by performing etching in an oblique direction while rotating the Si substrate.

As a second method, there is a method including processing a metal substrate such as Ni using a cutting tool such as a diamond bit to produce a plurality of projections 12 in arrays on the front surface of the original plate 11.

Next, as illustrated in FIG. 8B, a mold 13 is produced using the original plate 11. In order to produce a normal mold 13, a method using Ni electroforming is used. Since the original plate 11 has the projections 12 having a cone or pyramid shape (for example, quadrangular pyramid) with a sharp tip end, the shape is accurately transferred to the mold 13, and the mold 13 can be peeled off from the original plate 11. Four methods are considered for manufacturing at a low cost.

A first method is a method in which after a silicone resin obtained by adding a curing agent to polydimethylsiloxane (PDMS, for example, SYLGARD 184 manufactured by Dow Corning Corporation) is allowed to flow to the original plate 11 and cured by being heat-treated at 100° C., the mold 13 is peeled off from the original plate 11. A second method is a method in which after a UV-curable resin that is cured by ultraviolet irradiation is allowed to flow to the original plate 11 and irradiated with ultraviolet rays in a nitrogen atmosphere, the mold 13 is peeled off from the original plate 11. A third method is a method in which after a material obtained by dissolving a plastic resin such as polystyrene or polymethylmethacrylate (PMMA) in an organic solvent is allowed to flow to the original plate 11 coated with a peeling agent, and is dried to volatilize the organic solvent for curing, the mold 13 is peeled off from the original plate 11. A fourth method is a method in which a reversed product is made by Ni electroforming.

Accordingly, a mold 13 is produced in Which needle-shaped recesses 15 having a reversal shape of the projections 12 of the original plate 11 are arranged two-dimensionally. The mold 13 produced in this manner is illustrated in FIG. 8C. In any of the three methods, the mold 13 can be easily produced any number of times.

Figure 9A:
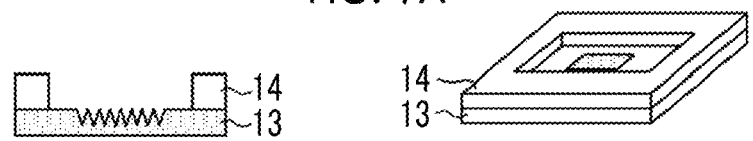
FIG. 9A is a perspective view of a mold on which a frame is provided.
Figure 9B:
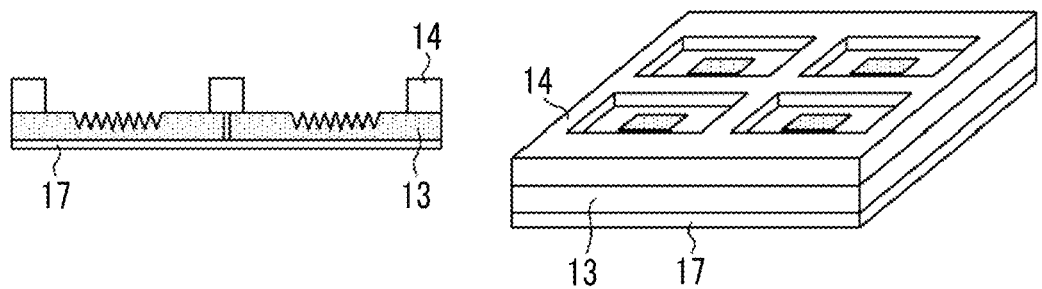
FIG. 9B is a perspective view of molds on which a frame is provided.

FIGS. 9A and 9B are drawings in which a frame 14 is installed on the mold 13 manufactured in FIG. 8C. FIG. 9A is a drawing in which the frame 14 is installed on the periphery of the front surface of the mold 13. FIG. 9B is a drawing in which a frame 14 is provided on the periphery and on the inside of a plurality of molds 13 put together. By providing the frame 14, it is possible to prevent a solution in which a polymer resin is dissolved (hereinafter, also referred to as "polymer solution") from flowing to the outside of the mold 13 in a case where a functional film is formed with a desired thickness.

At this time, a step between the mold 13 and the frame 14 is preferably 50 μm to 10 μm. The form of FIGS. 8A to 8C has a configuration in which the mold 13 and the frame 14 can be separated from each other. However, it may have a configuration in which the mold and the frame are formed integrally with each other. In a case of a separation-type configuration, the frame 14 can be detached in a drying step or a peeling-off step after a filling step.

Figure 10:
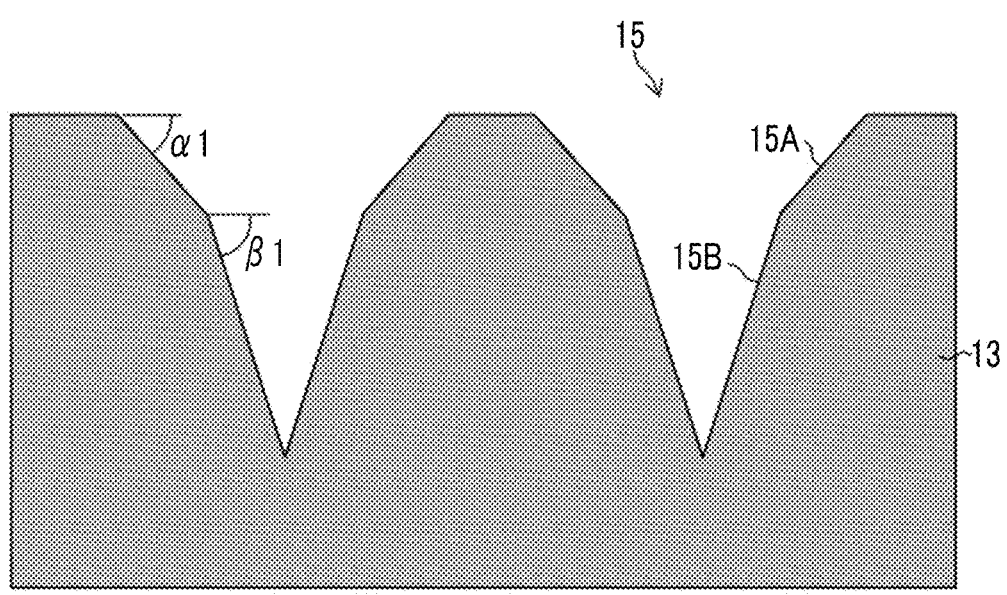
FIG. 10 is a partially enlarged view of the mold manufactured in FIGS. 8A to 8C.

As illustrated in FIG. 9B, the plurality of molds 13 is put together on a substrate 17 using an adhesive. The frame 14 is installed on the periphery and on the inside of the molds 13 put together, FIG. 10 is a partially enlarged view of the mold 13. The needle-shaped recess 15 is provided with a tapered inlet portion 15A that is narrowed in a depth direction from the front surface of the mold 13 and a tip end recess 15B that is tapered in the depth direction. An angle α1 of the taper of the inlet portion 15A basically corresponds to the angle α formed between the side surface of the frustum portion and the sheet portion in the transdermal absorption sheet. The angle β1 of the taper of the tip end recess 15B basically corresponds to the angle β formed between the side surface of the needle portion and the upper base of the frustum portion.

Figure 11:
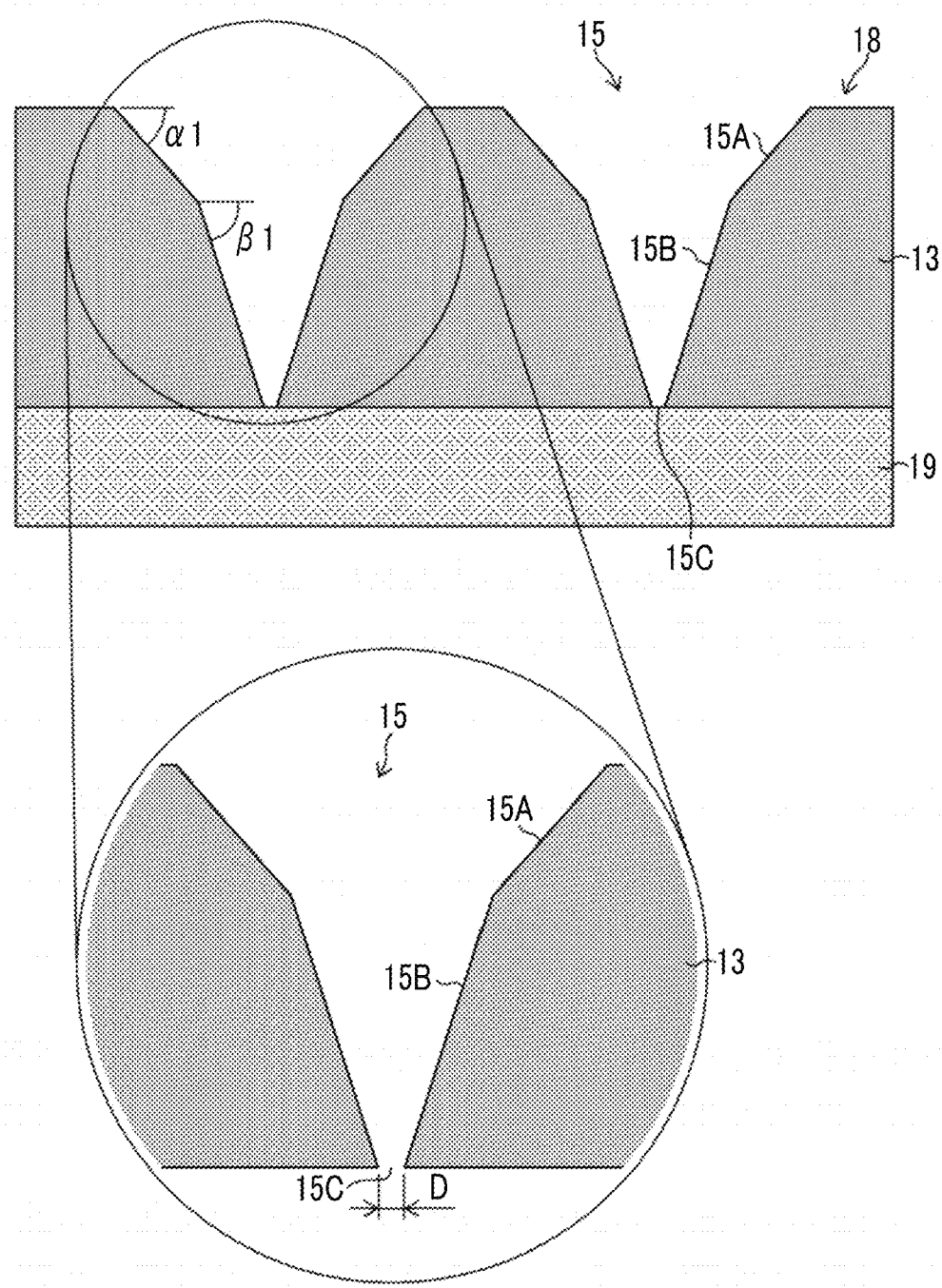
FIG. 11 is a partially enlarged view of the mold manufactured in FIGS. 8A to 8C.

FIG. 11 illustrates a more preferred embodiment of a mold composite 18 in performing a method of manufacturing a transdermal absorption sheet. As illustrated in FIG. 11, the mold composite 18 is formed of a mold 13 in which a through hole 15C is formed at a tip end of a needle-shaped recess 15 and a gas permeable sheet 19 that is bonded to the side of the through hole 15C of the mold 13 and is made of a material that is gas permeable, but is not liquid permeable. Through the through hole 15C, the tip end of the needle-shaped recess 15 communicates with the atmosphere via the gas permeable sheet 19. The expression "tip end of the needle-shaped recess 15" means a side that is tapered in a depth direction of the mold 13 and is opposite to a drug solution or base solution filling side.

Using such a mold composite 18, only the air present in the needle-shaped recess 15 can be bled from the needle-shaped recess 15 via the through hole 15C without permeation of a transdermal absorption material solution filled in the needle-shaped recess 15. Transferability in a case where the shape of the needle-shaped recess 15 is transferred to the transdermal absorption material is improved, and thus it is possible to form a sharper needle-shaped projection.

A diameter D (diameter) of the through hole 15C is preferably in a range of 1 to 50 μm, By adjusting the diameter within this range, air bleeding is easily performed, and the tip end portion of the needle-shaped projection of the transdermal absorption sheet is allowed to have a sharp shape. As the gas permeable sheet 19 made of a material that is gas permeable, but is not liquid permeable, for example, POREFLON (registered trademark in japan, Sumitomo Electric Industries, Ltd.) can be preferably used.

As the material for use in the mold 13, an elastic material or a metallic material can be used. Among these, an elastic material is preferred, and a material having high gas permeability is more preferred. The oxygen permeability representative for the gas permeability is preferably greater than $1\times10^{-12}$ (mL/s·m·Pa), and more preferably greater than $1\times10^{-10}$ (mL/s·m·Pa). By adjusting the gas permeability within the above range, the air present in the needle-shaped recess 15 of the mold 13 can be removed from the mold 13. It is possible to manufacture a transdermal absorption sheet with few defects. Specific examples of such a material include materials obtained by melting a silicone resin (for example, SYLGARD 184 or 1310ST), a UV-curable resin, or a plastic resin (for example, polystyrene or polymethylmethacrylate (PMMA)) and materials obtained by dissolving any of the above resins in a solvent. Among these, silicone rubber-based materials can be preferably used since these are durable in transfer by repeated pressurization and have good peelability from the material. Examples of the metallic material include Ni, Cu, Cr, Mo, W, Ir, Tr, Fe, Co, MgO, Ti, Zr, Hf, V, Nb, Ta, α-aluminum oxide, zirconium oxide, stainless steel (STAVAX), and alloys thereof. As the material of the frame 14, the same material as that of the mold 13 can be used.

(Polymer Solution)

A polymer solution that is used in this embodiment and is a solution in which a polymer resin is dissolved will be described.

In this embodiment, the polymer solution containing a predetermined amount of a drug is referred to as a polymer solution containing a drug or a solution containing a drug, and the polymer solution not containing a predetermined amount of a drug is referred to as a polymer solution not containing a drug or a solution not containing a drug, if necessary. In addition, the polymer solution containing a predetermined amount of drug is referred to as a drug solution, and the polymer solution not containing a predetermined amount of a drug is referred to as a base solution. Whether a predetermined amount of a drug is contained is determined based on whether medicinal effects are exhibited when puncture is performed on a body surface. Accordingly, the expression "containing a predetermined amount of a drug" means containing the drug in an amount such that medicinal effects are exhibited when puncture is performed on a body surface. In addition, the expression "not containing a predetermined amount of a drug" means that the drug is not contained in an amount such that medicinal effects are exhibited, and the range of the amount of the drug includes a range from 0, indicating that the drug is not contained at all, to an amount in which medicinal effects are not exhibited.

As the material of the resin polymer used in the polymer solution, a biocompatible resin is preferably used. As such a resin, saccharides such as glucose, maltose, pullulan, chondroitin sulfate, sodium hyaluronate, and hydroxyethyl starch, proteins such as gelatin, polylactates, and biodegradable polymers such as a lactic acid-glycollic acid copolymer are preferably used. Among these, gelatin-based materials have adhesiveness with many base materials and have a high gel strength as a material to be gelated. Thus, the gelatin-based materials can be preferably used during a peeling-off step to be described below since these can be closely attached to the base material to allow the polymer sheet to be peeled off from the mold using the base material. The concentration of the resin is preferably adjusted such that 10% to 50% by mass of the resin polymer is contained in the polymer solution not containing a drug, though the concentration depends on the material. In addition, a solvent used for dissolution may be other than hot water as long as it has volatility, and methyl ethyl ketone (MEK), alcohol, or the like can be used. In the solution in which the polymer resin is dissolved, a drug to be supplied to the inside of a body can concurrently be dissolved in accordance with the application. The polymer concentration of the polymer solution containing a drug (in a case where the drug itself is a polymer, the concentration of the polymer excluding the drug) is preferably 0% to 30% by mass.

As a method of preparing the polymer solution, in a case where a water-soluble polymer (gelatin or the like) is used, a water-soluble powder may be dissolved in water and a. drug may be added thereto. Otherwise, a water-soluble polymer powder may be added and dissolved in a liquid in which a drug is dissolved. In a case where a material that is difficult to dissolve in water is used, it may be dissolved by heating. The temperature can be appropriately selected depending on the type of the polymer material, but the material is preferably heated at a temperature of approximately 60° C. or lower. The viscosity of the solution in which the polymer resin is dissolved is preferably 100 Pa·s or less, and more preferably 10 Pa·s or less in the solution containing a drug. The viscosity is preferably 2,000 Pa·s or less, and more preferably 1,000 Pa·s or less in the solution not containing a drug. The solution is easily injected into the needle-shaped recess of the mold by appropriately adjusting the viscosity of the solution in which the polymer resin is dissolved. For example, the viscosity of the solution in which the polymer resin is dissolved can be measured using a tube-type viscometer, a drop-type viscometer, a rotational viscometer, or a vibration-type viscometer.

(Drug)

The drug that is contained in the polymer solution is not limited as long as it functions as a drug. Particularly, the drug is preferably selected from a peptide, a protein, a nucleic acid, a polysaccharide, a vaccine, a medical compound belonging to a water-soluble low-molecular-weight compound, or a cosmetic component.

(Method of Manufacturing Transdermal Absorption Sheet)

Figure 12:
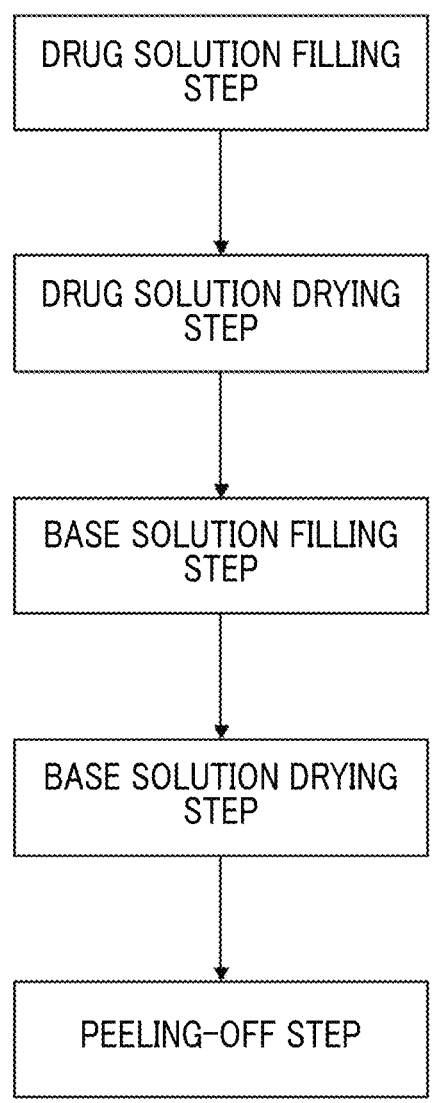
FIG. 12 is a flow diagram of a method of manufacturing a transdermal absorption sheet.

As illustrated in FIG. 12, the method of manufacturing a transdermal absorption sheet of this embodiment includes at least five steps, that is a drug solution filling step, a drug solution drying step, a base solution filling step, a base solution drying step, and a peeling-off step in this order. In the base solution filling step, for example, the solution is filled while an air bubble is incorporated under a normal temperature condition (15° C. to 25° C.), and the base solution drying step is performed in an environment with a temperature of 1° C. to 10° C.

The inventors have found that by performing the base solution drying step in an environment with a temperature of 1° C. to 10° C., the size of the air bubble incorporated in the base solution filling step can be controlled, and the air bubble is thus easily disposed in the needle portion.

In an environment with a temperature of 1° C. to 10° C., by increasing the solubility of the gas in the polymer solution constituting the base solution, the air bubble with a diameter of 1 to 150 µm incorporated in the base solution filling step under a normal temperature condition can be controlled to have a diameter of 1 to 100 µm. It is possible to suppress the disappearance of the air bubble by controlling the diameter of the air bubble to 1 µm or greater. In addition, by controlling the diameter of the air bubble to 100 µm or less, the movement of the air bubble by buoyancy is suppressed, and the air bubble can be controlled to stay at the boundary between the first layer and the second layer.

Figure 13:
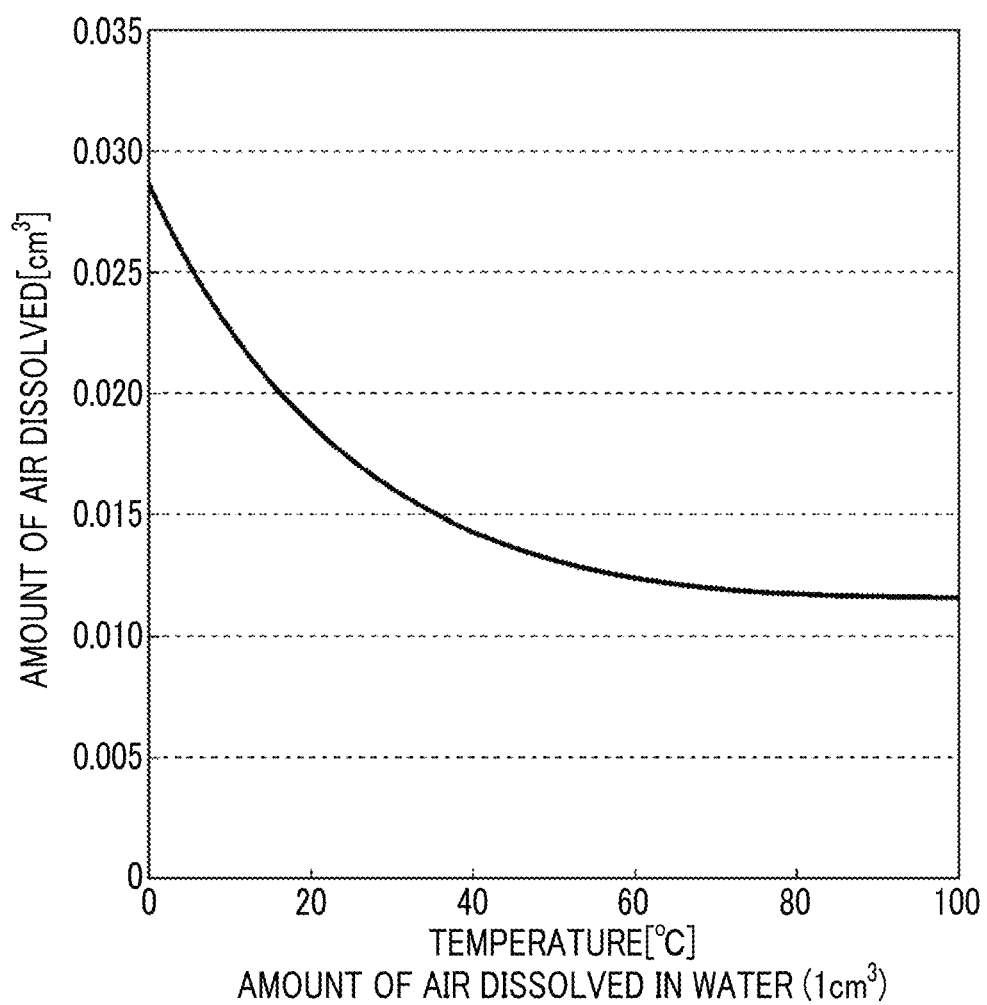
FIG. 13 is a graph illustrating the relationship between the temperature and the solubility of a gas with respect to 1 cm$^3$ of water.

FIG. 13 is a graph illustrating the relationship between the temperature and the solubility of the gas with respect to 1 $cm^3$ of water. The vertical axis represents the volume of the gas dissolved in water under 1 atm, and the horizontal axis represents the temperature. According to the graph of FIG. 13, an increase in the solubility when the temperature is 1° C. to 10° C. can be understood. In a case where the base solution drying step is performed at a temperature of 1° C. to 10° C., the solubility is increased, and the size of the air bubble can be reduced. The temperature range is preferably 1° C. to 10° C., and more preferably 2° C. to 8° C.

In order to perform the base solution drying step in an environment with a temperature of 1° C. to 10° C., for example, the base solution drying step may be performed in a thermostatic chamber or a thermostatic tank. In addition, the temperature range may be controlled by performing the drug solution filling step and the drug solution drying step in a thermostatic chamber or a thermostatic tank. If necessary, the relative humidities of the drug solution filling step, the drug solution drying step, the base solution filling step, and the base solution drying step may be controlled.

In the base solution drying step, for example, only a region where the base solution remains in a liquid state can be locally cooled using a chiller, a pettier device, or the like.

According to the method of manufacturing a transdermal absorption sheet of this embodiment, it is possible to suppress the generation of a large air bubble causing a loss in the peeling-off step or a puncture error In addition, it is possible to suppress the generation of unintended air bubble and the expanding and disappearance of air bubble, that occur in the base solution drying step. In addition, it is possible to suppress diffusion of the first layer containing a drug to the second layer not containing a drug by the presence of the air bubble.

(Drug Solution Filling Step)

Figure 14A:
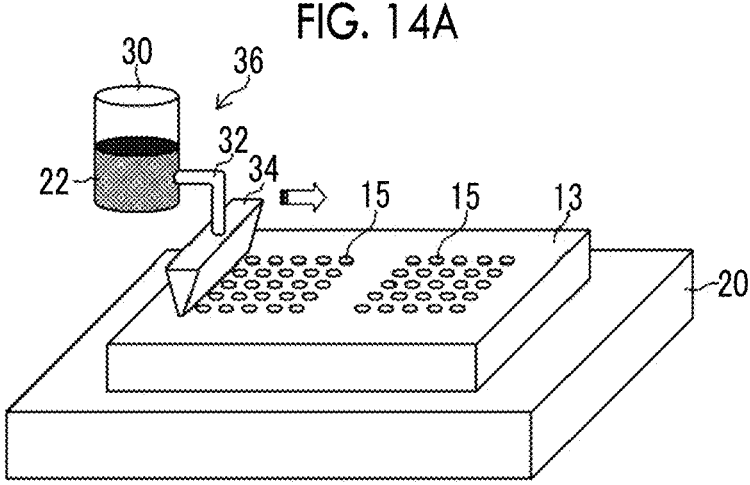
FIG. 14A is a schematic diagram illustrating a step of filling the needle-shaped recesses of the mold with a drug solution.

A method of manufacturing a transdermal absorption sheet using the mold 13 will be described. As illustrated in FIG. 14A, the mold 13 having the needle-shaped recesses 15 arranged two-dimensionally is disposed on a base 20. In the mold 13, two sets of the needle-shaped recesses 15 of 5×5 arranged two-dimensionally are formed. A liquid supply device 36 is prepared that has a liquid feed tank 30 storing a drug solution 22 that is a polymer solution containing a predetermined amount of a drug, a pipe 32 connected to the liquid feed tank 30, and a nozzle 34 connected to a tip end of the pipe 32. The drug solution 22 is discharged from a tip end of the nozzle 34.

Figure 15:
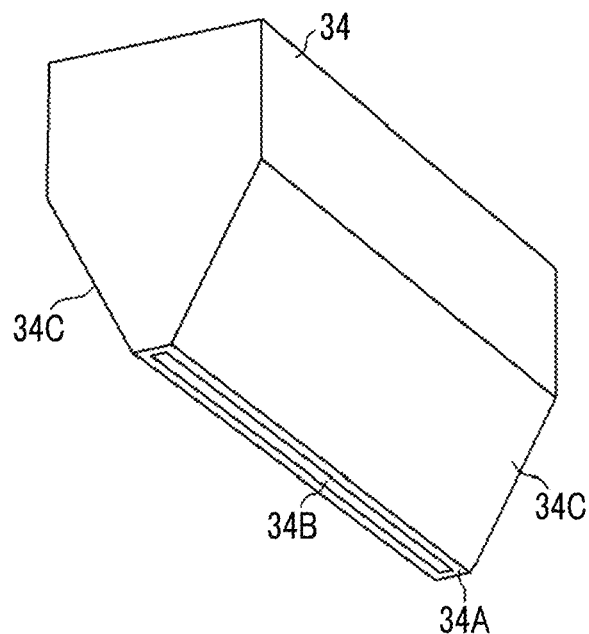
FIG. 15 is a perspective view illustrating a tip end of a nozzle.

FIG. 15 shows a schematic perspective view of the tip end portion of the nozzle. As illustrated in FIG. 15, the nozzle 34 is provided with a lip portion 34A having a flat surface on the tip end side thereof, a slit-shaped opening portion 34B, and two inclined surfaces 34C expanding in a direction in which these are separated from the opening portion 34B along the lip portion 34A. Through the slit-shaped opening portion 349, for example, it is possible to simultaneously fill a plurality of needle-shaped recesses 15 configuring one row with the drug solution 22. The size (length and width) of the opening portion 34B is appropriately selected in accordance with the number of needle-shaped recesses 15 to be filled at one time, By increasing the length of the opening portion 349, the number of needle-shaped recesses 15 to be filled with the drug solution 22 at one time can be increased. Accordingly, productivity can be improved.

Figure 16:
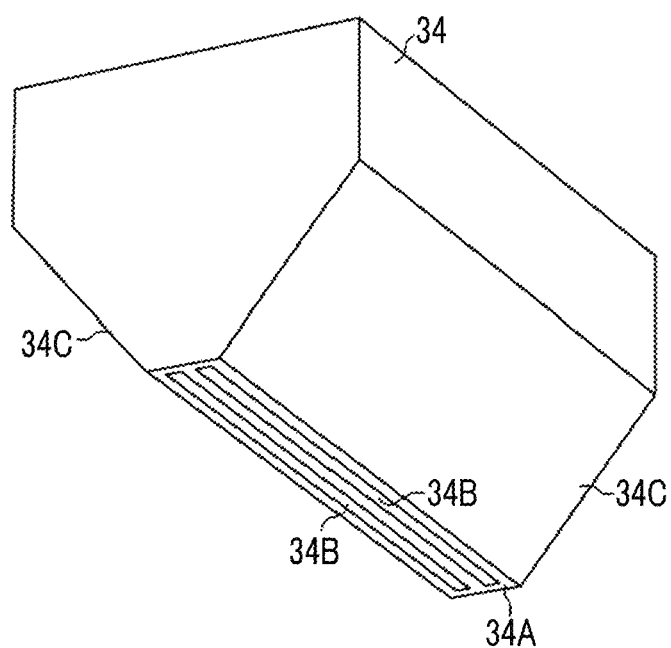
FIG. 16 is a perspective view illustrating a tip end of a different nozzle.

FIG. 16 shows a schematic perspective view of a tip end portion of a different nozzle. As illustrated in FIG. 16, a nozzle 34 is provided with a lip portion 34A having a flat surface on the tip end side thereof, two slit-shaped opening portions 34B, and two inclined surfaces 34C expanding in a direction in which these are separated from the opening portions 34B along the lip portion 34A. Through the two opening portions 34B, for example, it is possible to simultaneously fill a plurality of needle-shaped recesses 15 configuring two rows with the drug solution 22 containing a drug.

As the material for use in the nozzle 34, an elastic material or a metallic material can be used. Examples thereof include TEFLON (registered trademark in Japan), stainless steel (SUS), and titanium.

Figure 14B:
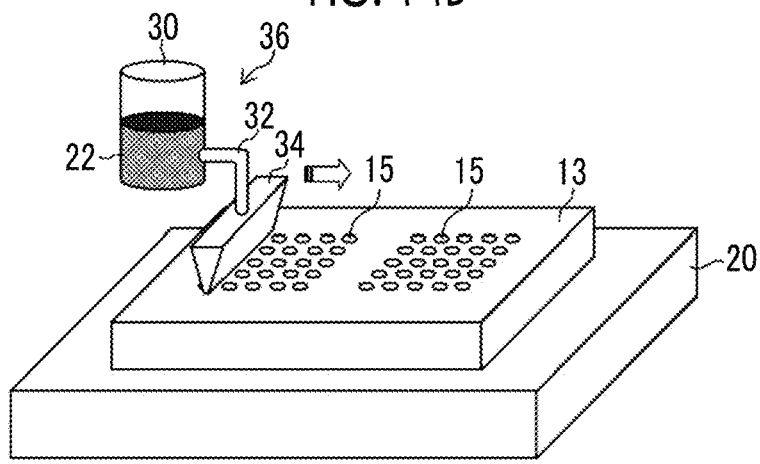
FIG. 14B is a schematic diagram illustrating a step of filling the needle-shaped recesses of the mold with a drug solution.

The filling step will be described with reference to FIG. 14B. As illustrated in FIG. 14B, the opening portion 34B of the nozzle 34 is adjusted to be positioned above the needle-shaped recesses 15. The nozzle 34 that discharges the drug solution 22 is pressed to the mold 13, and thus the lip portion 34A of the nozzle 34 and the front surface of the mold 13 are brought into contact with each other. The drug solution 22 is supplied to the mold 13 from the liquid supply device 36, and thus the needle-shaped recesses 15 are filled with the drug solution 22 from the opening portion 3413 of the nozzle 34. In this embodiment, a plurality of needle-shaped recesses 15 configuring one row is filled with the drug solution 22 simultaneously. However, the invention is not limited thereto, and the needle-shaped recesses 15 can be filled one by one. In addition, using the nozzle 34 illustrated in FIG. 16, the plurality of needle-shaped recesses 15 configuring the plurality of rows can be simultaneously filled with the drug solution 22 every plural rows.

In a case where the mold 13 is made of a gas permeable material, the drug solution 22 can be sucked by suction from a rear surface of the mold 13, and thus it is possible to promote the filling of the needle-shaped recesses 15 with the drug solution 22.

Figure 14C:
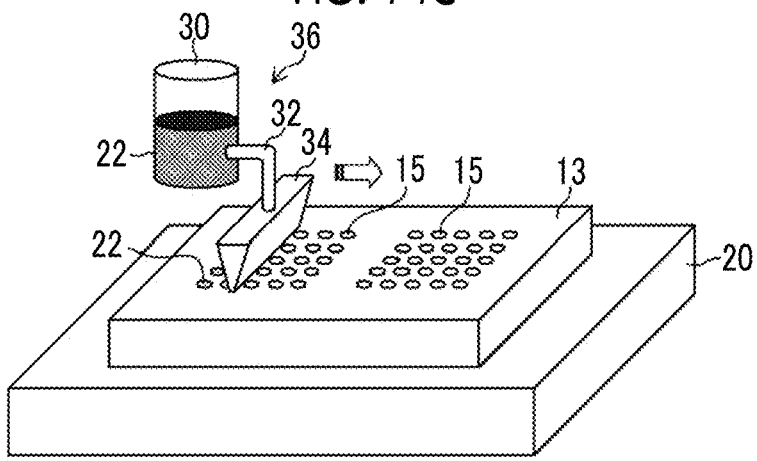
FIG. 14C is a schematic diagram illustrating a step of filling the needle-shaped. recesses of the mold with a drug solution.

After the tilling step with reference to FIG. 14B, as illustrated in FIG. 14C, the liquid supply device 36 is relatively scanned in a direction perpendicular to a length direction of the opening portion 34B while the lip portion 34A of the nozzle 34 and the front surface of the mold 13 are brought into contact with each other. The nozzle 34 performs scanning on the mold 13, and the nozzle 34 is moved to a needle-shaped recess 15 that is not filled with the drug solution 22. The opening portion 34B of the nozzle 34 is adjusted to be positioned above the needle-shaped recess 15. In this embodiment, the example in which the nozzle 34 is scanned has been described, but the mold 13 may be scanned.

Since the nozzle 34 is scanned on the mold 13 with the contact between the lip portion 34A of the nozzle 34 and the front surface of the mold 13, the nozzle 34 can scrape off the drug solution 22 remaining on the front surface other than the needle-shaped recesses 15 of the mold 13. Accordingly, it is possible to prevent the drug solution 22 containing a drug from remaining on regions other than the needle-shaped recesses 15 of the mold 13. In this embodiment, the nozzle 34 is disposed such that the inclined surfaces 34C are positioned to be perpendicular to the scanning direction shown by the arrow. Accordingly, the nozzle 34 can perform smooth scanning on the mold 13.

In order to reduce damage on the mold 13 and suppress deformation by compression of the mold 13 as much as possible, the degree of pressing the nozzle 3410 the mold 13 during scanning is preferably controlled. For example, a pressing force of the nozzle 34 to the mold 13 and a pressing distance of the nozzle 34 to the mold 13 are preferably controlled. In addition, in order to prevent the drug solution 22 from remaining on regions other than the needle-shaped recesses 15 of the mold 13, it is desirable that the material of at least one of the mold 13 or the nozzle 34 is flexible and elastically deformed.

By repeating the filling step of FIG. 14B and the moving step of FIG. 14C, the needle-shaped recesses 15 of 5×5 arranged two-dimensionally are filled with the drug solution 22. In a case where the needle-shaped recesses 15 of 5×5 arranged two-dimensionally are filled with the drug solution 22, the liquid supply device 36 is moved to adjacent needle-shaped recesses 15 of 5×5 arranged two-dimensionally, and the filling step of FIG. 14B and the moving step of FIG. 14C are repeated. The adjacent needle-shaped recesses 15 of 5×5 arranged two-dimensionally are also filled with the drug solution 22.

Regarding the above-described filling step and scanning step, an embodiment (1) in which the needle-shaped recesses 15 are filled with the drug solution 22 while the nozzle 34 is scanned, or an embodiment (2) in which the nozzle 34 is temporarily stopped on the needle-shaped recesses 15 during the scanning of the nozzle 34 and filled with the drug solution 22, and after the filling, the nozzle 34 is scanned again may be applied. The lip portion 34A of the nozzle 34 is pressed to the front surface of the mold 13 between the filling step and the scanning step. The amount of the drug solution 22 to be discharged from the liquid supply device 36 is preferably the same as the total volume of the plurality of needle-shaped recesses 15 of the mold 13. The drug solution 22 is prevented from remaining on the front surface other than the needle-shaped recesses 15 of the mold 13 to be filled, and the loss of the drug can be reduced.

Figure 17:
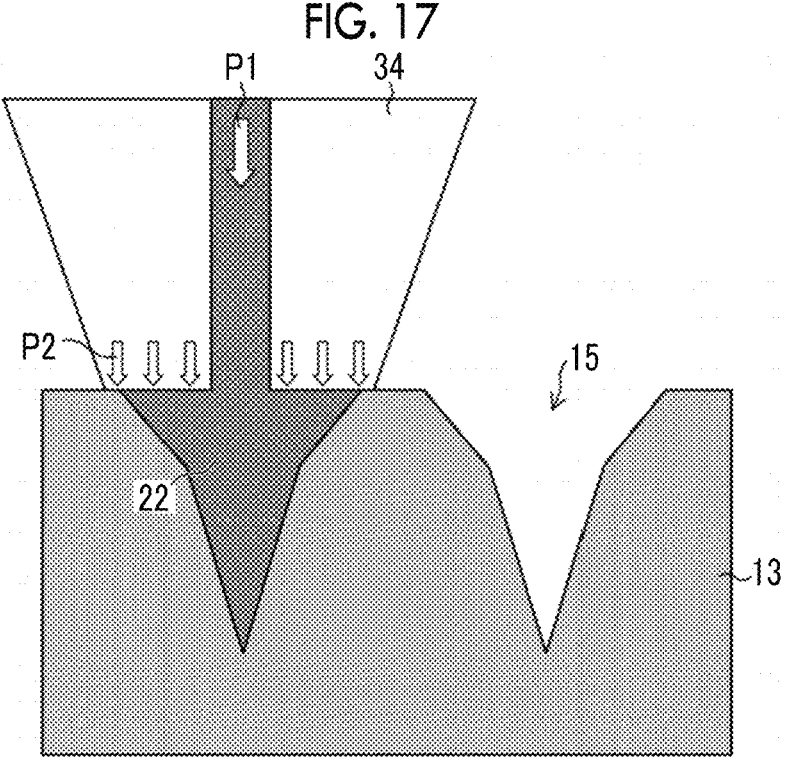
FIG. 17 is a partially enlarged view of a tip end of the nozzle and the mold during

FIG. 17 is a partially enlarged view of the tip end of the nozzle 34 and the mold 13 during the filling of the needle-shaped recess 15 with the drug solution 22. As illustrated in FIG. 17, it is possible to promote the filling of the needle-shaped recesses 15 with the drug solution 22 by applying a pressure P1 into the nozzle 34. Furthermore, when the needle-shaped recesses 15 are filled with the drug solution 22, a pressing force P2 for bringing the nozzle 34 into contact with the front surface of the mold 13 is preferably equal to or greater than the pressure P1 in the nozzle 34. By satisfying the equation: pressing force P2≥pressure P1, it is possible to suppress leakage of the drug solution 22 from the needle-shaped recess 15 to the front surface of the mold 13.

Figure 18:
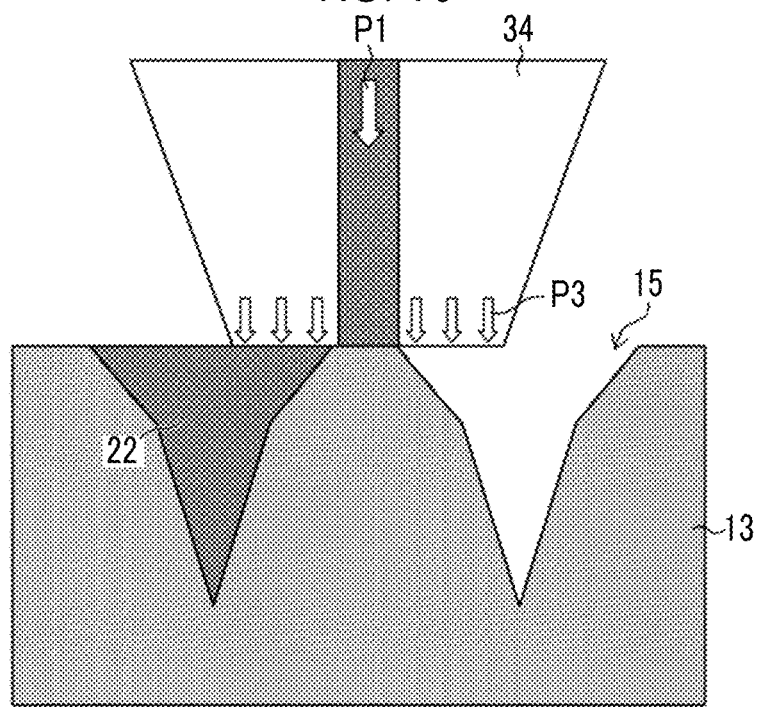
FIG. 18 is a partially enlarged view of the tip end of the nozzle and the mold during scanning.

FIG. 18 is a partially enlarged view of the tip end of the nozzle 34 and the mold 13 during the movement of the nozzle 34. When the nozzle 34 is relatively scanned with respect to the mold 13, a pressing force P3 for bringing the nozzle 34 into contact with the front surface of the mold 13 is preferably smaller than the pressing force P2 for bringing the nozzle 34 into contact with the front surface of the mold 13 during the filling. This is because damage on the mold 13 is reduced, and deformation by compression of the mold 13 is suppressed.

The lip portion 34A of the nozzle 34 is preferably parallel to the front surface of the mold 13. The posture of the nozzle 34 may be controlled by providing a joint driving mechanism at a mounting portion of the nozzle 34.

Figure 19:
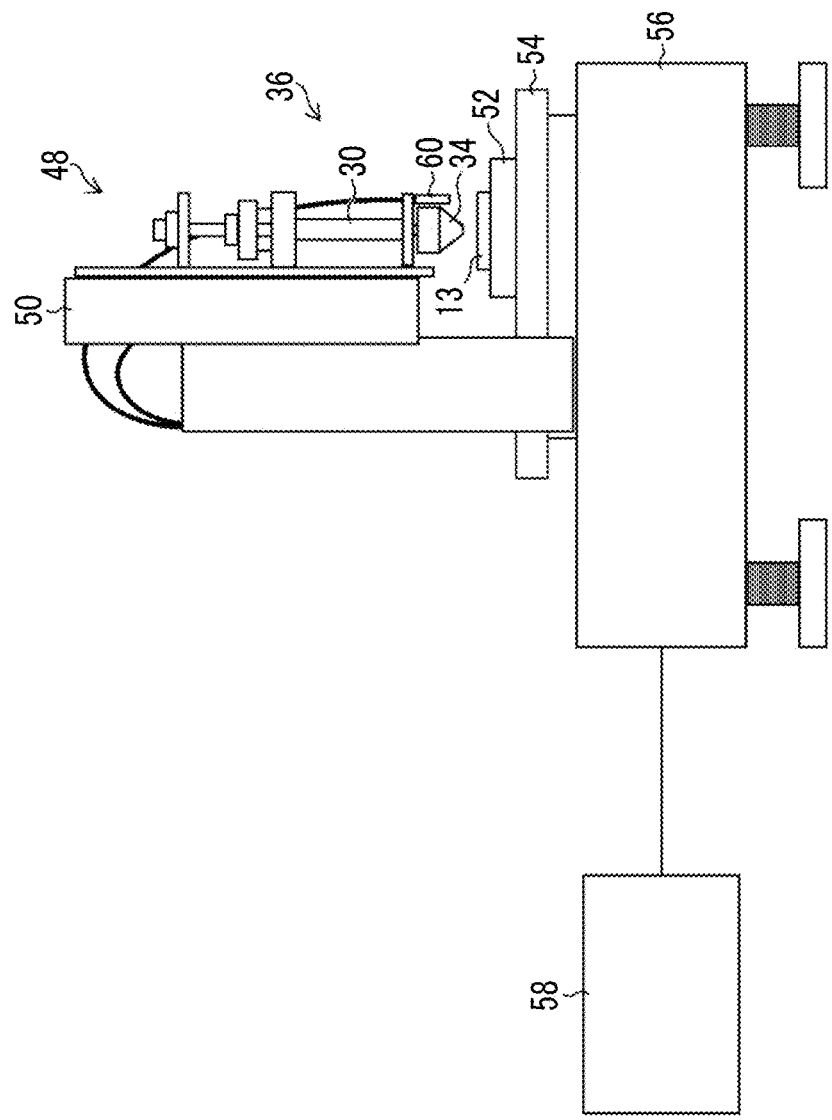
FIG. 19 is a schematic configuration diagram of a drug solution filling apparatus.

The pressing force and/or the pressing distance of the nozzle 34 to the mold 13 is/are preferably controlled by driving the nozzle 34 in a Z-axis direction in accordance with the front surface shape of the mold 13. FIG. 19 is a schematic configuration diagram of a drug solution filling apparatus 48 capable of controlling the pressing force and/or the pressing distance. The drug solution filling apparatus 48 has a liquid supply device 36 that has a liquid feed tank 30 storing a drug solution and a nozzle 34 mounted on the liquid feed tank 30, a Z-axis driving portion 50 that drives the liquid feed tank 30 and the nozzle 34 in the Z-axis direction, a suction base 52 for placing the mold 13 thereon, a X-axis driving portion 54 that drives the suction base 52 in a X-axis direction, a stand 56 that supports the device, and a control system 58.

A case of controlling a pressing force to be constant will be described. The Z-axis driving portion 50 brings the nozzle 34 close to the mold 13 up to Z-coordinates in which a desired pressing force is obtained. While the nozzle 34 brought into contact with the mold 13 is scanned by the X-axis driving portion 54, the drug solution 22 is discharged while Z-axis coordinate control is performed such that the pressing force becomes constant. The contact pressure measuring method is not particularly limited, but for example, various load cells can be used, for example, under the suction base 52 or in place of the suction base 52. The load cell means a measuring instrument capable of measuring a force for compression in a thickness direction. The pressing force is an arbitrary pressure within a range of 1 to 1,000 kPa with respect to the mold 13, and is preferably controlled to be constant.

A case of controlling a pressing distance to be constant will be described. Before contact with the nozzle 34, the front surface shape of the mold 13 is previously measured. While the nozzle 34 brought into contact with the mold 13 is scanned by the X-axis driving portion 54, the drug solution 22 is discharged while the value obtained by performing Z-axis coordinate offset such that a desired pressing distance is provided with respect to the front surface shape of the mold 13 is fed back to the Z-axis driving portion 50.

The shape measuring method is not particularly limited. For example, an optical measuring instrument such as a non-contact-type laser displacement meter 60 or a contact-type (probe-type) step profiler can be used. Furthermore, the posture of the nozzle 34 in a slit direction may be controlled in accordance with the front surface shape of the mold 13.

The pressing distance is preferably controlled within a range of 1% to 15% with respect to the thickness of the mold 13. Through the operation with the control of the distance between the nozzle 34 and the mold 13 in the Z-axis direction by the Z-axis driving portion 50 in accordance with the shape of the mold 13, the compression deformation rate is uniformized, and thus the accuracy of the filling amount can be improved.

Regarding the control of the pressing force and the pressing distance, the pressing force is preferably controlled in a case where the pressing distance is small, and the pressing distance is preferably directly controlled in a case where the pressing distance is large.

Figure 20:
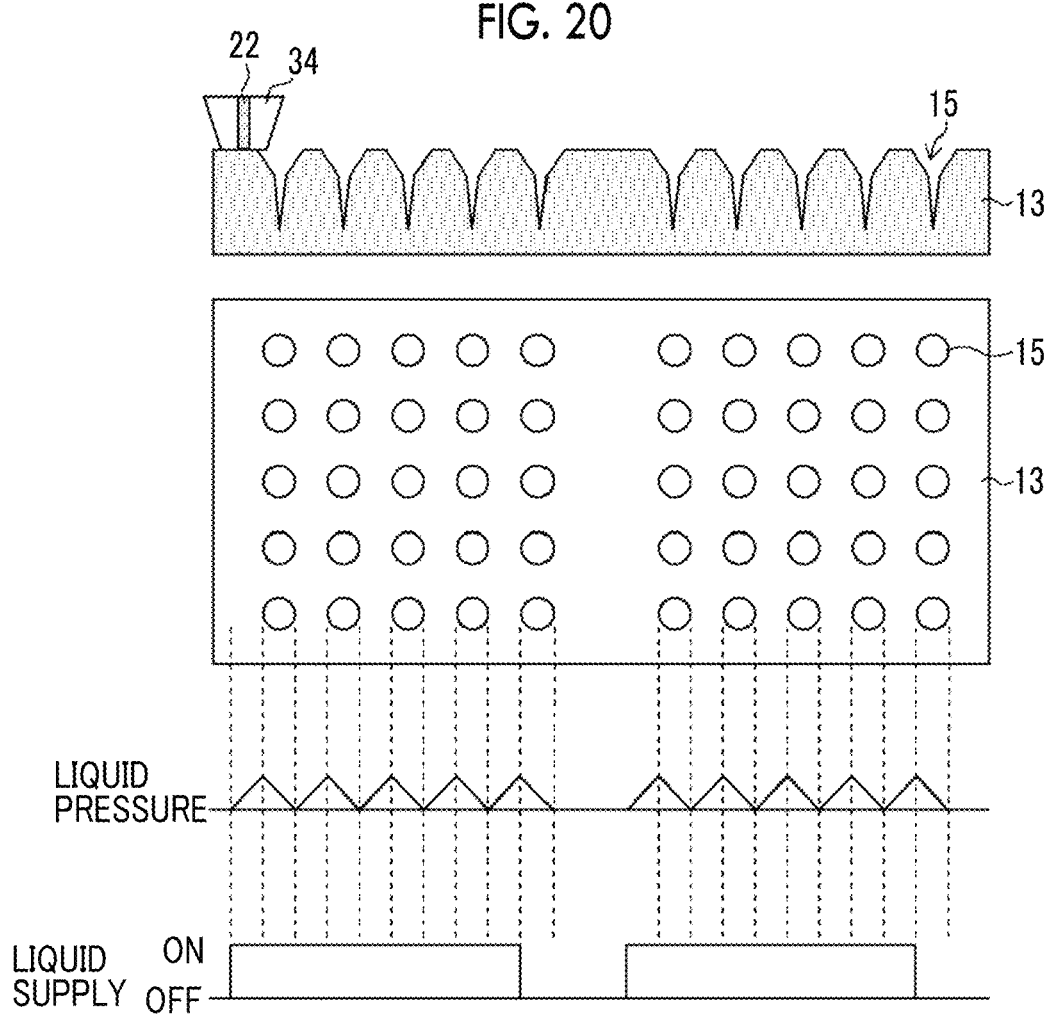
FIG. 20 is an explanation drawing illustrating the relationship between the liquid pressure in the nozzle and the supply of the solution containing a drug.

FIG. 20 is an explanation drawing illustrating the relationship between the liquid pressure in the nozzle and the supply of the solution containing a drug. As illustrated in FIG. 20, the supply of the drug solution 22 is started before the nozzle 34 is positioned above the needle-shaped recesses 15. The reason for this is to securely fill the needle-shaped recesses 15 with the drug solution 22. Until the filling of the plurality of needle-shaped recesses 15 of 5×5 is completed, the drug solution 22 is continuously supplied to the mold 13. The supply of the drug solution 22 to the mold 13 is stopped before the nozzle 34 is positioned above needle-shaped recesses 15 in the fifth row. Therefore, it is possible to prevent the drug solution 22 from overflowing from the needle-shaped recesses 15. The liquid pressure in the nozzle 34 increases in a region where the nozzle 34 is not positioned above the needle-shaped recesses 15 when the supply of the drug solution 22 is started. When the nozzle 34 is positioned above the needle-shaped recesses 15, the needle-shaped recesses 15 are filled with the drug solution 22, and the liquid pressure in the nozzle 34 decreases. That is, the liquid pressure repeatedly changes.

When the filling of the plurality of needle-shaped recesses 15 of 5×5 is completed, the nozzle 34 is moved to a plurality of adjacent needle-shaped recesses 15 of 5×5. Regarding the liquid supply, the supply of the drug solution 22 is preferably stopped when the nozzle is moved to the plurality of adjacent needle-shaped recesses 15 of 5×5. There is a distance between the needle-shaped recesses 15 in the fifth row and the needle-shaped recesses 15 in the next first row. In a case where the drug solution 22 is continuously supplied therebetween during the scanning of the nozzle 34, the liquid pressure in the nozzle 34 may excessively increase. As a result, the drug solution 22 may flow to regions other than the needle-shaped recesses 15 of the mold 13 from the nozzle 34. In order to suppress this problem, the supply of the drug solution 22 is preferably stopped.

The tip end of the nozzle 34 is preferably used after being cleaned when the drug solution filling is performed. This is because the accuracy of the filling amount of the drug solution 22 is reduced in a case where a material adheres to the surface of the lip portion 34A of the nozzle 34 before filling. In general, wiping using non-woven cloth is performed for cleaning. During wiping, the cleaning can be effectively performed in a case where non-woven cloth is permeated with water, a solvent, or the like. After filling with the drug solution 22, the drug solution may remain on the front surface of the mold 13 when the nozzle 34 is separated from the mold 13. By performing suck back control for suction of the drug solution from the opening portion 343 of the nozzle 34 after completion of the filling of the needle-shaped recesses 15, a surplus of the drug solution 22 can be sucked, and the liquid remaining on the front surface of the mold 13 can thus be reduced.

In this embodiment, the drug solution filling step is preferably performed in an environment with a temperature of 1° C. to 10° C. Accordingly, an air bubble having a diameter of approximately several tens to 100 µm can be dissolved in the polymer solution constituting the drug solution 22 even in a case where an air bubble is incorporated in the drug. solution 22 in the liquid feed tank 30, the pipe 32, the pipe connection portion, the nozzle 34, or the like, or a case where the air in the needle-shaped recess 15 is incorporated in the drug solution 22 when the needle-shaped recess 15 of the mold 13 is filled with the drug solution In the drug solution filling step, the drug solution can be sucked from the through hole 15C using the mold 13 illustrated in FIG. 10 to till the needle-shaped recess 15 with the drug solution 22. This is because it is not particularly preferable that an air bubble is incorporated in the drug solution 22 since a variation occurs in the content of the drug. The drug solution filling step is preferably performed at a temperature of 1° C. to 10° C. since an air bubble can be dissolved in the polymer solution constituting the drug solution 22.

When the filling of the needle-shaped recesses 15 with the drug solution 22 is completed, the process proceeds to the drug solution drying step, the base solution filling step, the base solution drying step, and the peeling-off step.

Figure 21A:
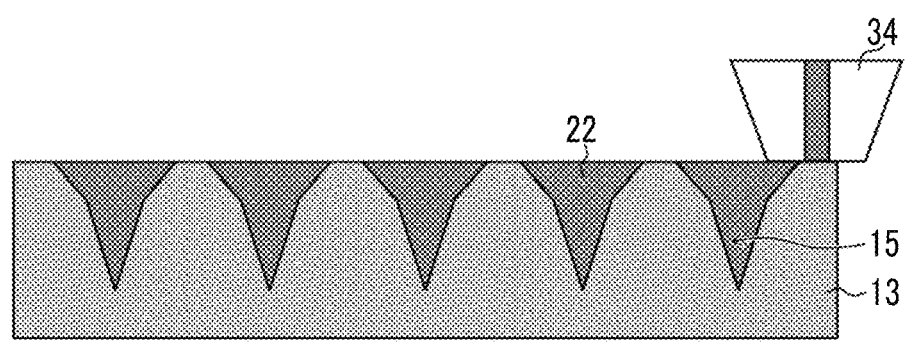
FIG. 21A is a schematic diagram illustrating a part of a different step of manufacturing a transdermal absorption sheet.

As illustrated in FIG. 21A, the needle-shaped recesses 15 of the mold 13 are filled with the drug solution 22 from the nozzle 34 in the drug solution filling step. The drug solution filling step is performed using the above-described method.

(Drug Solution Drying Step)

Figure 21B:
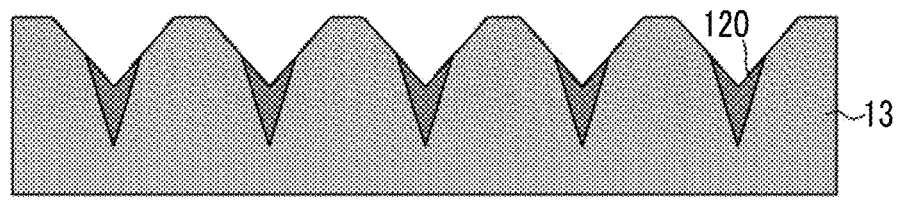
FIG. 21B is a schematic diagram illustrating a part of a different step of manufacturing a transdermal absorption sheet.

As illustrated in FIG. 21B, in the drug solution drying step, the drug solution 22 is dried and solidified, and thus first layers 120 containing a drug are formed in the needle-shaped recesses 15.

The drug solution drying step is a step of drying the drug solution 22 filled in the needle-shaped recesses 15 of the mold 13 and localizing the drug solution at tie tip ends of the needle-shaped recesses 15. In this embodiment, the drug solution drying step is preferably performed in an environment with a temperature of 1° C. to 10° C. In a case where the drug solution drying step is performed in an environment with a higher temperature than 10° C., the gas (air) dissolved in the polymer solution of the drug solution 22 in the drug solution filling step may turn into an air bubble due to an increase in temperature. In a case where the amount of the gas dissolved is small, no air bubble is generated. However, the increase in temperature may cause an unexpected air bubble defect. Accordingly, the generation of the air bubble defect can be reduced by performing the drug solution drying step in an environment with a temperature of 1° C. to 10° C.

In addition, by optimizing the drying rate with the control of the temperature and humidity conditions of the drug solution drying step, it is possible to reduce the adhesiveness of the drug solution 22 to a wall surface of the mold 13 of the needle-shaped recesses 15, and the drying proceeds while the drug solution 22 is collected at the tip ends of the needle-shaped recesses 15 by drying. For example, in an environment of 23° C./40 to 60% RH, the drying rate is high, and thus the drug solution 22 may adhere to a wall surface of the mold 13 of the needle-shaped recesses 15 and it may be difficult to localize the drug solution 22 at the tip ends of the needle-shaped recesses 15.

The drying rate of the drug solution 22 can be reduced by perforating the drug solution drying step in an environment with a temperature of 1° C. to 10° C. Accordingly, the drug solution 22 can be localized at the tip ends of the needle-shaped recesses 15 without adhesion of the drug solution 22 to a wall surface of the mold 13. In the drug solution drying step in an environment with a temperature of 1° C. to 10° C., in a case where the humidity is high, the drying rate of the drug solution 22 is reduced, and thus it leads to a reduction in productivity. Accordingly, in a case where the drug solution drying step is performed in an environment with a temperature of 1° C. to 10° C., an environment with a relative humidity of 1% to 59% is preferably provided, and an environment with a relative humidity of 21% to 39% is more preferably provided. In an environment with a relative humidity range of 1% to 59% at a temperature of 1° C. to 10° C., it is possible to achieve high productivity and the localization of the drug solution 22 at the tip ends of the needle-shaped recesses 15 at the same time.

In order to provide an enviromnent with a relative humidity of 1% to 59%, for example, the drug solution drying step is preferably performed in a thermostatic chamber or a thermostatic tank having a humidity adjustment function.

The drug solution 22 is preferably dried in a calm state in the drug solution drying step. Uneven drying occurs in a case where the drug solution 22 is directly exposed to non-uniform wind. This is because, in a portion exposed to strong wind, the drying rate may be increased, the drug solution 22 may adhere to a wall surface of the mold 13, and thus the localization of the drug solution 22 at the tip ends of the needle-shaped recesses 15 may be disturbed, In order to realize the drying in a calm state, for example, a windshield is preferably installed. The windshield is installed so as not to directly expose the mold 13 to wind. As the windshield, a physical obstacle such as a lid, a hood, a screen, a fence, or the like is preferably installed since this is a simple method. In addition, when the windshield is installed, a vent hole or the like is preferably secured such that the installation space for the mold 13 is not in an enclosed state. In a case where the installation space is in an enclosed state, water vapor in the enclosed space may be saturated, and the drying of the drug solution 22 may not proceed. The vent hole is preferably formed such that the passage of vapor is possible, and is more preferably covered with a water vapor permeable film or the like to stabilize the air flow in the windshield The drying time is appropriately adjusted in consideration of the shape of the needle-shaped recess 15, the arrangement and the number of the needle-shaped recesses 15, the type of the drug, the filling amount and the concentration of the drug solution 22, and the like.

The calm state refers to a case where the wind speed is 0.5 m/s or less, including a state in which there is no wind at all. The reason why the wind speed is within this range is that uneven drying rarely occurs.

In the drug solution drying step, the drug solution 22 is solidified by being dried, and is reduced in size compared with that when the filling with the drug solution 22 is performed. Accordingly, in the peeling-off step, the first layer 120 can be easily peeled off from the needle-shaped recess 15 of the mold 13.

(Base Solution Filling Step)

Figure 21C:
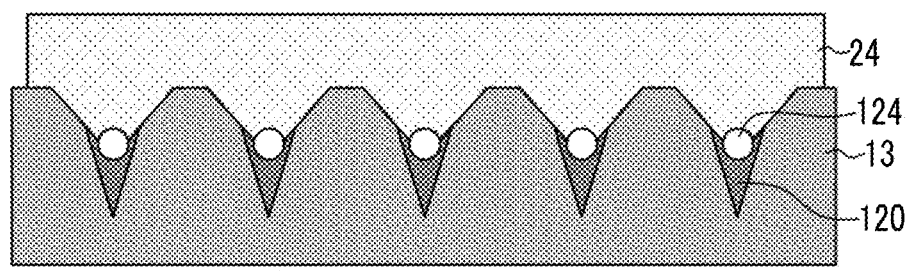
FIG. 21C is a schematic diagram illustrating a part of a different step of manufacturing a transdermal absorption sheet.

Next, as illustrated in FIG. 21C, the first layer 120 containing a predetermined amount of a drug is coated with a base solution 24 that is a polymer solution not containing a predetermined amount of a drug using a dispenser, and the needle-shaped recesses 15 are filled with the base solution 24. The base solution 24 in an amount larger than the spaces of the needle-shaped recesses 15 fills the needle-shaped recesses. Bar coating, spin coating, coating using a spray, or the like can be applied in place of coating using the dispenser.

In this embodiment, the air bubble generated in the liquid feed tank, the pipe, the pipe connection portion, the dispenser, or the like, or the air present in the needle-shaped recess 15 when the needle-shaped recess 15 of the mold 13 is filled with the base solution 24 is incorporated in the base solution 24 as an air bubble 124.

Even in a case where the tip end portion of the needle-shaped recess 15 of the mold 13 has a through hole 15C, the through hole 15C is blocked since the first layer 120 is solidified. Therefore, the air bubble 124 can be formed near the boundary between the first layer 120 and the base solution 24 when the filling with the base solution is performed. The size of the air bubble 124 incorporated in the base solution 24 depends on the shape of the needle-shaped recess 15. Under a normal temperature condition (15° C. to 25° C.), an air bubble 124 having a diameter of 1 to 150 μm is mainly formed and incorporated in the base solution 24.

Figure 22A:
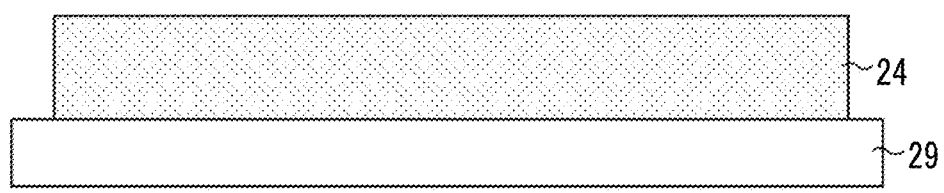
FIG. 22A is a schematic diagram illustrating apart of a different step of manufacturing a transdermal absorption sheet.
Figure 22B:
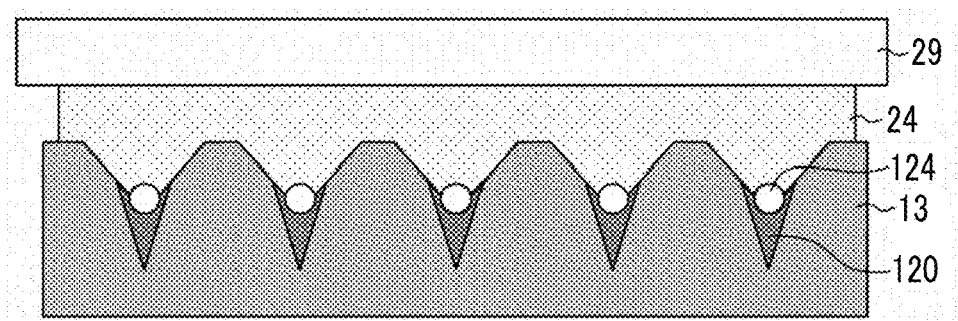
FIG. 22B is a schematic diagram illustrating apart of a different step of manufacturing a transdermal absorption sheet.

Next, another embodiment of the base solution filling step will be described. As illustrated in FIG. 22A, a separate support 29 is coated with a base solution 24 that is a solution not containing a drug. The support 29 is not limited, and for example, polyethylene, polyethylene terephthalate, polycarbonate, polypropylene, acrylic resin, triacetylcellulose, or the like can be used. Next, as illustrated in FIG. 22B, the base solution 24 formed on the support 29 is superposed on the mold 13 in which the first layer 120 is formed in the needle-shaped recess 15. Therefore, the needle-shaped recess 15 is filled with the base solution 24.

In this embodiment, the base solution filling step includes two steps, that is, coating the support 29 with the base solution 24 and superposing the base solution 24 on the support 29 on the mold 13. During the superposition, the air present in the needle-shaped recess 15 is incorporated in the base solution 24 as the air bubble 124, (Base Solution Drying Step)

Figure 21D:
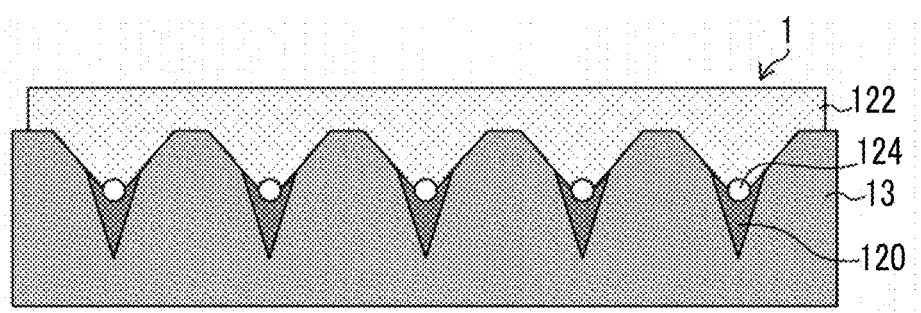
FIG. 21D is a schematic diagram illustrating a part of a different step of manufacturing a transdermal absorption sheet.

Next, as illustrated in FIG. 21D, a second layer 122 not containing a predetermined amount of a drug is formed on the first layer 120 by drying and solidifying the base solution 24. A polymer sheet 1 having the first layer 120 and the second layer 122 is manufactured.

In this embodiment, the base solution drying step is performed in an environment with a temperature of 1° C. to 10° C. In a case where the base solution drying step is performed in an environment with a higher temperature than 10° C., the gas (air) dissolved in the polymer solution of the base solution 24 in the base solution filling step may turn into a new air bubble due to an increase in temperature. In addition, the air bubble 124 existing already may expand. In a case Where the amount of the gas dissolved is small, no air bubble is generated. However, the increase in temperature may cause an unexpected air bubble defect. Accordingly, the generation of the unexpected air bubble and the expanding of the air bubble can be suppressed by performing the base solution drying step in an environment with a temperature of 1° C. to 10° C.

In the base solution drying step, in order to suppress the movement of the air bubble 124 to an unexpected position, the installation is preferably performed such that buoyancy to the air bubble acts in a direction of the tip end of the needle-shaped recess 15. For example, buoyancy can be applied upward to the air bubble 124 by positioning the tip end of the needle-shaped recess 15 on the upper side in the vertical direction.

The first layer 120 containing a drug is present in a solidified state at the tip end portion of the needle-shaped recess 15. In a case where no air bubble 124 is present when the filling with the base solution 24 is performed, there is a problem in that the base solution 24 permeates through the first layer 120 and causes diffusion of the first layer 120 to the base solution 24. In this embodiment, since the air bubble 124 is present, the air bubble 124 serves as a physical barrier. Accordingly, permeation of the base solution 24 through the first layer 120 can be suppressed, and as a result, diffusion of the first layer 120 to the base solution 24 can be suppressed.

In the base solution drying step in an environment with a temperature of 1° C. to 10° C., in a case where the humidity is high, the drying rate of the base solution 24 is reduced, and thus it leads to a reduction in productivity. Accordingly, in a case where the base solution drying step is performed in an environment with a temperature of 1° C. to 10° C., an environment with a relative humidity of 1% to 59% is preferably provided, and an environment with a relative humidity of 21% to 39% is more preferably provided. In an environment with a relative humidity range of 1% to 59% at a temperature of 1° C. to 10° C., it is possible to improve productivity.

In order to provide an environment with a relative humidity of 1% to 59%, for example, the base solution drying step is preferably performed in a thermostatic chamber or a thermostatic tank having a humidity adjustment function.

In order to promote the drying of the base solution 24, 0.1 to 10 mils of wind is preferably allowed to blow The base solution 24 does not contain a predetermined amount of a drug. Accordingly, even when uneven drying occurs, the influence thereof is small.

In the base solution drying step, the volume of the base solution 24 is reduced by drying. In a case where the base solution 24 is closely attached to the mold 13 during the drying, the reduction in volume occurs in the thickness direction of the sheet, and thus the thickness is reduced.

In a case where the base solution 24 is peeled off from the mold 13 during the drying, the polymer sheet 1 shrinks also in a plane direction. Accordingly, it may be distorted or may curl. In a case where the polymer sheet 1 is peeled off from the mold 13 in a state in which the base solution 24 in the needle-shaped recesses 15 is not sufficiently dried, defects such as breaking or bending of the shape of the needle-shaped projections of the polymer sheet 1 may be easily generated. Accordingly, the polymer sheet 1 is preferably not peeled off from the mold 13 during the drying. In addition, on the rear surface (the surface opposite to the surface having the needle-shaped projections formed therein) of the polymer sheet 1, a layer that shrinks to the same extent as the front surface having the needle-shaped projections may be formed in order to suppress curling. For example, the same polymer solution as that on the front surface side is coated on the rear surface side to form a layer having a thickness confirmed previously to have a curling suppression effect.

(Peeling-Off Step)

Figure 23:
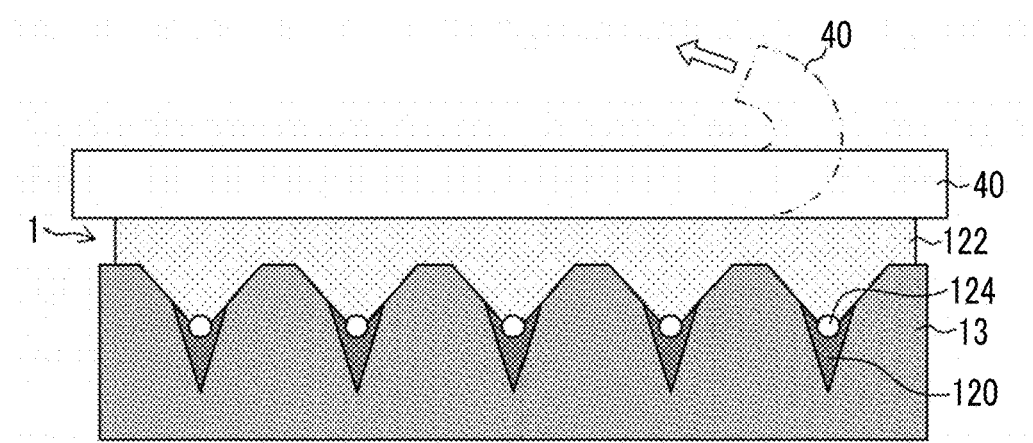
FIG. 23 is an explanation drawing illustrating a peeling-off step.
Figure 24:
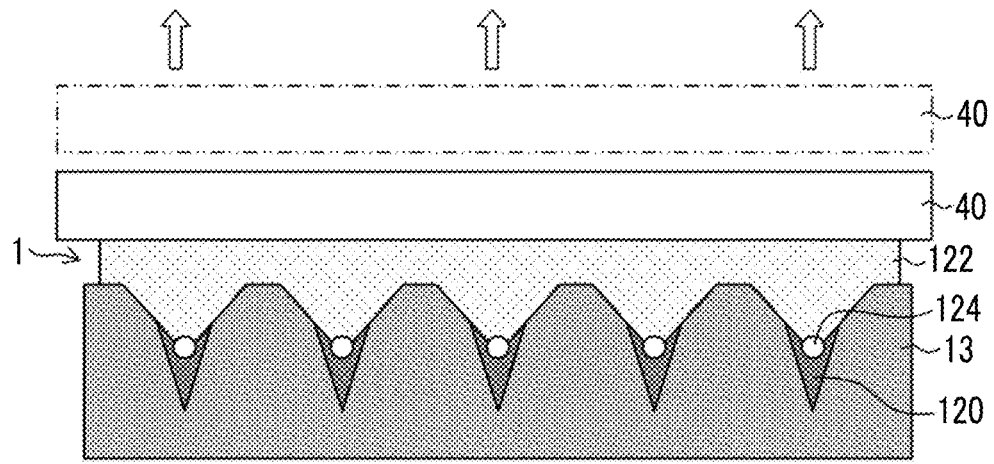
FIG. 24 is an explanation drawing illustrating a different peeling-off step.

The method of peeling off the polymer sheet 1 from the mold 13 is not limited. It is desirable that the needle-shaped projections do not bend or are not broken during peeling-off. Specifically, as illustrated in FIG. 23, a sheet-shaped base material 40 in which an adhesive layer having adhesive properties is formed is adhered to the polymer sheet 1, and then the base material 40 can be peeled off to be turned over from an end portion. However, in this method, the needle-shaped projections may bend. Therefore, a method in which a sucker (not shown) is installed on the rear surface of the polymer sheet 1 and it is possible to vertically lift the polymer sheet while sucking it by air as illustrated in FIG. 24 can be applied. A transdermal absorption sheet 100 is manufactured by peeling off the polymer sheet 1 from the mold 13.

Usually, in a case where a structure as a needle-shaped projection having a high aspect ratio is peeled off from the mold 13 as in this embodiment, a strong stress is applied due to a large contact area therebetween. The fine needle that is the needle-shaped projection is broken and remains in the needle-shaped recess 15 without being peeled off from the mold 13, and a transdermal absorption sheet to be produced has defects. In this embodiment, the mold 13 is preferably made of a material that is very easily peelable. In addition, the mold 13 is made of a soft material having high elasticity, and thus the stress that is applied to the fine needle during peeling-off can be relaxed.

(Deaeration Step)

The drug solution 22 and/or the base solution 24 is/are preferably subjected to deaeration before the drug solution filling step and/or before the base solution filling step. Through deaeration, the air bubbles contained in the drug solution 22 and the base solution 24 can be removed before the filling of the needle-shaped recesses 15 of the mold 13. For example, in the deaeration step, air bubbles having a diameter of 100 μm to several millimeters are removed. By subjecting at least one of the drug solution 22 or the base solution 24 to deaeration, dissolution of the air bubble in the polymer solution can be promoted.

Examples of the deaeration method include (1) a method of exposing the drug solution 22 under a reduced pressure environment for 1 to 15 minutes, (2) a method of subjecting a container storing the drug solution 22 to ultrasonic vibration for 5 to 10 minutes, (3) a method of applying ultrasonic waves while exposing the drug solution 22 under a reduced pressure environment, and (4) a method of substituting the dissolved gas with helium by sending a helium gas into the drug solution 22. Any of the deaeration methods (1) to (4) can be applied to the base solution 24 also.

EXAMPLES

Hereinafter, the invention will be described in more detail using examples of the invention. The materials, amounts, ratios, treatment contents, treatment procedures, and the like shown in the following examples can be appropriately changed without departing from the gist of the invention. The following specific examples are therefore to be considered in all respects as illustrative and not restrictive.

Example 1

(Production of Mold)

Figure 25:
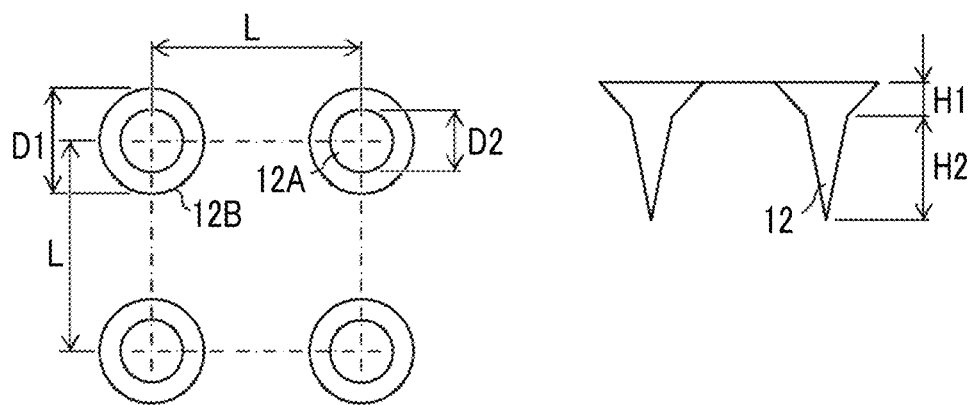
FIG. 25 shows a plan view and a side view of an original plate.

Projections 12 each having a needle-shaped structure in which a cone 12A having a diameter D2 of 300 μm and a height H1 of 500 μm was formed on a truncated circular cone 12B having a diameter D1 of 500 μm in a bottom surface and a height H2 of 150 μm as illustrated in FIG. 25 were subjected to grinding in two-dimensional arrays of 10 rows×10 columns with a pitch L of 1,000 μm on a surface of a smooth Ni plate having a side of 40 mm, and thus an original plate 11 was produced. On this original plate 11, a silicone rubber (SILASTIC MDX4-4210 manufactured by Dow Coming Corporation) film with a thickness of 0.6 mm was formed. The Film was thermally cured in a state in which the conical tip end portions of the original plate 11 were projected by 50 μm from the film surface, and was peeled off. Accordingly, a reversed silicone rubber product having through holes having a diameter of approximately 30 μm was produced. A planar portion having a side of 30 mm in which needle-shaped recesses of 10 rows×10 columns arranged two-dimensionally were formed in a center portion of the reversed silicone rubber product was cut off and used as a mold. A surface in which the needle-shaped recesses had wide opening portions served as a front surface of the mid, and a surface having through holes (air bleed holes) having a diameter of 30 μm served as a rear surface of the mold.

(Preparation of Polymer Solution Containing Drug)

Hydroxyethyl starch (manufactured by Fresenius Kabi) was dissolved in water to prepare an aqueous solution of 8%. To this aqueous solution, 2% by weight of human serum albumin (manufactured by Wako Pure Chemical Industries, Ltd.) as a drug and 0.01% by weight of EVANS BLUE dye (manufactured by Wako Pure Chemical Industries, Ltd.) were added to prepare a drug solution containing a drug.

(Preparation of Solution Not containing Drug)

Chondroitin sulfate (manufactured by Manilla Nichiro Corporation) was dissolved in water to prepare an aqueous solution of 40% as a solution not containing a drug.

Hereinafter, the drug solution filling step, the drug solution drying step, and the base solution drying step were performed in an environment with a temperature of 10° C., and the base solution tilling step was performed in an environment with a temperature of 15° C.

(Drug Solution Filling Step and Drug Solution Drying Step)

A drug solution filling apparatus is provided with a driving portion that has a X-axis driving portion and Z-axis driving portion controlling relative position coordinates of the mold and the nozzle, a liquid supply device (super small amount fixed-quantity dispenser SMP-III manufactured by Musashi Engineering, Inc.) on which the nozzle can be mounted, a suction base to which the mold is fixed, a laser displacement gauge (HL-C201A manufactured by Panasonic Corporation) that measures a front surface shape of the mold, a load cell (LCX-A-500N manufactured by Kyowa. Electronic Instruments Co., Ltd.) that measures a nozzle pressing pressure, and a control system that controls the Z axis based on data of measurement values of the front surface shape and the pressing pressure.

A gas permeable film (POREFLON FP-010 manufactured by Sumitomo Electric Industries, Ltd.) having a side of 15 mm was placed on the flat suction base, and the mold was installed thereon such that the front surface thereof was positioned on the upper side. The gas permeable film and the mold were fixed to the vacuum board by pressure reduction with a suction pressure of 90 kPa. gauge pressure in a rear surface direction of the mold.

A SUS (stainless steel) nozzle having the shape illustrated in FIG. 15 was prepared, and a slit-shaped opening portion having a length of 12 mm and a width of 0.2 mm was formed at the center of a lip portion having a length of 20 mm and a width of 0.2 mm. This nozzle was connected to the drug solution tank. The drug solution tank and the nozzle were filled with 3 mL of a solution containing a drug. The nozzle was adjusted such that the opening portion was parallel to a first row of a plurality of needle-shaped recesses formed in the front surface of the mold. The nozzle was pressed to the mold at a pressure (pressing force) of 0.14 kgf/cm$^2$ (1.4 N/cm$^2$) at a position spaced apart from the first row with an interval of 2 mm therebetween in a direction opposite to a second row While being pressed, the nozzle was moved at 1 mm/sec in a direction perpendicular to a length direction of the opening portion while the Z axis was controlled such that the pressing force changed within ±0.05 kgf/cm² (0.49 N/cm²). Simultaneously, by the liquid supply device, the solution containing a drug was discharged from the opening portion for 10 seconds at 0.31 µL/sec. The movement of the nozzle was stopped at a position spaced apart from a tenth row of the plurality of needle-shaped recesses arranged two-dimensionally with an interval of 2 mm therebetween in a direction opposite to a ninth row, and the nozzle was separated from the mold.

The mold filled with the drug solution was put and dried in a windshield (25 cm³) with an opening portion having a diameter of 5 mm. The windshield mentioned herein has a gas permeable film (POREFLON FP-010 manufactured by Sumitomo Electric Industries, Ltd.) mounted on the opening portion and is structured so as not to be directly exposed to wind to provide a calm state.

(Base Solution Filling Step and Base Solution Drying Step)

A polymer solution (base solution) not containing a drug was coated with a thickness of 75 µm on front and rear surfaces of a polyethylene terephthalate (PET) subjected to a hydrophilic treatment. The mold was filled with the drug solution was fixed to the suction base by suction. The front surface of the PET coated with the base solution was disposed to face the front surface of the mold, and the pressures in a gap between the PET and the mold and in a space on the side opposite to the mold of the PET were reduced for 2 minutes under the condition that the gauge pressure was 50 kPa. A sufficient vacuum state is not provided when the gauge pressure is 50 kPa. Accordingly, the air present in the needle-shaped recess is easily incorporated in the base solution as an air bubble. After the pressure reduction, the PET and the mold were attached to each other by releasing only the space on the side opposite to the mold of the PET to atmospheric pressure. After the contact state was maintained for 10 minutes, a material obtained by attaching the PET and the mold to each other in an integrated manner was dried.

(Peeling-Off Step)

The mold was peeled off from the polymer layer on the PET so as to be turned over from an end portion. On the PET, a transdermal absorption sheet with a three-dimensional arrangement structure that included a first layer containing a drug in which the human serum albumin was unevenly distributed at a tip end and a second layer not containing a drug was formed.

(Evaluation)

The amount of air bubble generated in the needle-shaped projection was evaluated. As an evaluation method, the transdermal absorption sheet was observed using a microscope (VHX-600 manufactured by Keyence Corporation). The air bubble size evaluation was performed on a plurality of transdermal absorption sheets produced, and the air bubble present in the needle had a size of 1 to 100 µm in any sheet. Among these, transdermal absorption sheets with needles in which the air bubble sizes were 1 µm, 25 µm, 50 µm, and 100 µm, respectively, were selected. In each sheet, only one needle was left and all other needles were removed. With the obtained transdermal absorption sheets, the effects thereof were compared according to the evaluation method in the following table.

Example 2

A transdermal absorption sheet was produced under the same conditions as in Example 1, except that the base solution drying step was performed in an enviromnent with a temperature of 5° C.

The amount of air bubble generated in the needle-shaped projection in the produced transdermal absorption sheet was evaluated. As an evaluation method, the transdermal absorption sheet was observed using a microscope (VI-IX-600 manufactured by Keyence Corporation). The air bubble size evaluation was performed on a plurality of transdermal absorption sheets produced, and the air bubble present in the needle-shaped projection had a size of 1 to 50 µm in any sheet.

Example 3

A transdermal absorption sheet was produced under the same conditions as in Example 1, except that the base solution diving, step was performed in an environment with a temperature of 1° C.

The amount of air bubble generated in the needle-shaped projection in the produced transdermal absorption sheet was evaluated. As an evaluation method, the transdermal absorption sheet was observed using a microscope (VHX-600 manufactured by Keyence Corporation). The presence or absence of air bubble was evaluated in a plurality of transdermal absorption sheets produced, and there were transdermal absorption sheets in which the air bubble was present in the needle-shaped projection. The air bubble size evaluation was performed, and the air bubble present in the needle-shaped projection had a size of 1 to 25 µm. Among the plurality of needle-shaped projections of one transdermal absorption sheet, needle-shaped projections in which an air bubble was present and needle-shaped projections in which no air bubble was present were shown.

(Evaluation Results)

Regarding the dissolution rate, needle-shaped projections were selected based on the air bubble size to puncture a rat skin. The lengths of the needle-shaped projections remaining in the skin after 10 minutes from the puncture were compared for evaluation. In regard to the transdermal absorption sheets having no air bubble, a case where the dissolution rate was high was evaluated as G, and a case where the dissolution rate was low was evaluated as NG Regarding the drug diffusion, using a polymer solution containing a drug to which 0.01% of EVANS BLUE was added, a transdermal absorption sheet was produced, and dye distribution of a side surface was observed using a microscope to evaluate a dye diffusion distance from a tip end of the needle.

In regard to the transdermal absorption sheets having no air bubble, a case where the diffusion rate was low was evaluated as G, and a case where the diffusion rate was high was evaluated as NG. Regarding the puncturing properties, needle-shaped projections were selected based on the air bubble size to puncture a rat skin. The lengths of the needle-shaped. projections remaining in the skin after 10 minutes from the puncture were compared for evaluation. A case where the needle was not broken was evaluated as G, and a case where the needle was broken was evaluated as NG From the lengths of the needle-shaped projections, it was confirmed that a needle-shaped projection containing an air bubble having a diameter of 1 µm to 50 µm was harder to break than a needle-shaped projection containing an air bubble having a diameter of 100 µm.

TABLE 1

| | Size of Air Bubble | | | |
|---|---|---|---|---|
| | 1 μm | 25 μm | 50 μm | 100 μm |
| Dissolution Rate | G | G | G | G |
| Drug Diffusion | G | G | G | G |
| Puncturing Properties | G | G | G | G |

EXPLANATION OF REFERENCES

13: MOLD
15: NEEDLE-SHAPED RECESS
22: DRUG SOLUTION
24: BASE SOLUTION
34: NOZZLE
34A: LIP PORTION
34B: OPENING PORTION
100: TRANSDERMAL ABSORPTION SHEET
110: NEEDLE-SHAPED PROJECTION
112: NEEDLE PORTION
114: FRUSTUM PORTION
116: SHEET PORTION
120: FIRST LAYER
122: SECOND LAYER

What is claimed is:

1. A transdermal absorption sheet comprising:
a flat plate-shaped sheet portion;
a plurality of frustum portions which are disposed on the sheet portion and in each of which a larger bottom surface is connected to the sheet portion; and
a plurality of tapered-shaped needle portions which are disposed on the plurality of frustum portions and in each of which a bottom surface is connected to a smaller bottom surface of the frustum portion,
wherein each of the plurality of needle portions includes a first layer containing a predetermined amount of a drug and a second layer not containing a predetermined amount of a drug, and
at least one of the plurality of needle portions contains an air bubble.

2. The transdermal absorption sheet according to claim 1, wherein the air bubble is disposed between the first layer and the second layer.

3. The transdermal absorption sheet according to claim 1, wherein the air bubble has a diameter of 1 μm to 50 μm.

4. The transdermal absorption sheet according to claim 1, wherein the needle portion has a cone shape.

5. The transdermal absorption sheet according to claim 1, wherein a tapered needle-shaped portion and a cylindrical body portion configure the needle portion.

6. The transdermal absorption sheet according to claim 1, wherein an angle a formed between a side surface of the frustum portion and a surface parallel to a front surface of the sheet portion is 10° to 60°.

7. The transdermal absorption sheet according to claim 1, wherein the frustum portion has a height of 10 μm to 1,000 μm.

8. The transdermal absorption sheet according to claim 1, wherein the drug is a peptide, a protein, a nucleic acid, a polysaccharide, a vaccine, a medical compound belonging to a water-soluble low-molecular-weight compound, or a cosmetic component.

9. A method of manufacturing a transdermal absorption sheet comprising, in this order:
a drug solution filling step of filling needle-shaped recesses of a mold having the needle-shaped recesses arranged two-dimensionally with a drug solution that is a polymer solution containing a predetermined amount of a drug;
a drug solution drying step of drying the drug solution filled in the needle-shaped. recesses to form a first layer containing a predetermined amount of a drug;
a base solution filling step of filling the needle-shaped recesses with a base solution that is a polymer solution not containing a predetermined amount of a drug on the first layer while incorporating an air bubble;
a base solution drying step of drying the base solution to form a second layer not containing a predetermined amount of a drug on the first layer; and
a peeling-off step of peeling off the first layer and the second layer from the mold,
wherein the base solution drying step is performed in an environment with a temperature of 1° C. to 10° C.

10. The method of manufacturing a transdermal absorption sheet according to claim 9, further comprising:
a step of subjecting the drug solution to deaeration before the drug solution filling step.

11. The method of manufacturing a transdermal absorption sheet according to claim 9
wherein the needle-shaped recess of the mold has a through hole at a tip end thereof.

12. The method of manufacturing a transdermal absorption sheet according to claim 9,
wherein in the drug solution drying step, the drying is performed in a calm state.

13. The method of manufacturing a transdermal absorption sheet according to claim 9,
wherein in the drug solution filling step, a nozzle that discharges the drug solution is pressed to the mold to perform scanning on the mold, and the needle-shaped recesses are filled with the drug solution from the nozzle while a pressing force of the nozzle with respect to the mold is controlled.

14. The method of manufacturing a transdermal absorption sheet according to claim 9,
wherein in the drug solution filling step, a nozzle that discharges the drug solution is pressed to the mold to perform scanning on the mold, and the needle-shaped recesses are filled with the drug solution from the nozzle while a pressing distance of the nozzle with respect to the mold is controlled.

15. The method of manufacturing a transdermal absorption sheet according to claim 9,
wherein in the drug solution filling step, the amount of the drug solution to be filled is equal to a total volume of the needle-shaped recesses.

* * * * *